US010160779B2

(12) United States Patent
Schöne et al.

(10) Patent No.: US 10,160,779 B2
(45) Date of Patent: Dec. 25, 2018

(54) SYNTHESIS OF PHOSPHORAMIDATES

(71) Applicant: Sandoz AG, Basel (CH)

(72) Inventors: Olga Schöne, Kundl (AT); Thorsten Wilhelm, Kundl (AT)

(73) Assignee: Sandoz AG (CH)

( * ) Notice: Subject to any disclaimer, the term of this patent is extended or adjusted under 35 U.S.C. 154(b) by 0 days.

(21) Appl. No.: 15/737,900

(22) PCT Filed: Jun. 22, 2016

(86) PCT No.: PCT/EP2016/064370
§ 371 (c)(1),
(2) Date: Dec. 19, 2017

(87) PCT Pub. No.: WO2016/207194
PCT Pub. Date: Dec. 29, 2016

(65) Prior Publication Data
US 2018/0298045 A1    Oct. 18, 2018

(30) Foreign Application Priority Data

Jun. 22, 2015   (EP) .................................... 15173155

(51) Int. Cl.
*C07F 9/6558*     (2006.01)
(52) U.S. Cl.
CPC ............................... *C07F 9/65586* (2013.01)
(58) Field of Classification Search
CPC ...................................................... C07F 9/6588
USPC ................................................ 536/26.8, 28.1
See application file for complete search history.

(56) References Cited

U.S. PATENT DOCUMENTS 8,563,530 B2 * 10/2013 Chang .................. C07H 19/207
514/47
2006/0241064 A1   10/2006 Roberts et al.
2010/0298257 A1   11/2010 Ross et al.

FOREIGN PATENT DOCUMENTS

| WO | 2006031725 A2 | 3/2006 |
| WO | 2010135569 A1 | 11/2010 |
| WO | 2011123645 A2 | 10/2011 |
| WO | 2014164533 A1 | 10/2014 |
| WO | 2016066283 A1 | 5/2016 |
| WO | 2016134054 A1 | 8/2016 |

OTHER PUBLICATIONS

International Search Report and Written Opinion for PCT/EP2016/064370, dated Sep. 28, 2016.

B. Capon et al. Introduction Historical and General Description of Neighboring Group Effects Plenum Press, New York 1973.
Brian Capon Neighboring Group Participation Chemistry Department Birkbeck College, London, Published Jan. 1, 1964.
Hiroyuki Hayakawa et al Reaction of Organometallic Reagents . . . Communications to the Editor, Chem. Pharm. Bull. 1987.
Peiyuan Wang et al An Efficient and Diastereoselective Synthesis of PSI-6130: A Clinically Efficacios Inhibitor of HCV NS5B Polymerase J. Org. Chem. Published on Jul. 30, 2009.

\* cited by examiner

*Primary Examiner* — Venkataraman Balasubramanian
(74) *Attorney, Agent, or Firm* — Luedeka Neely Group, P.C.

(57) ABSTRACT

A process for preparing a compound of formula (I) or a salt thereof, the process comprising providing a compound of formula (III) wherein PG is an inert electron withdrawing hydroxyl protecting group, reacting the compound of formula (III) with a fluorinating agent, obtaining a compound of formula (II) and deprotecting the compound of formula (II).

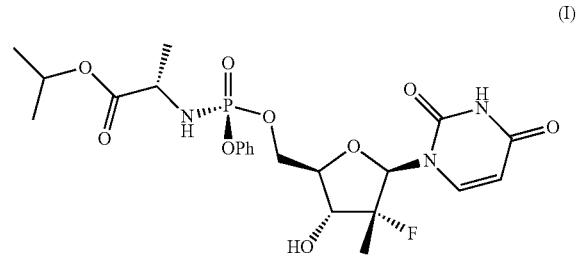

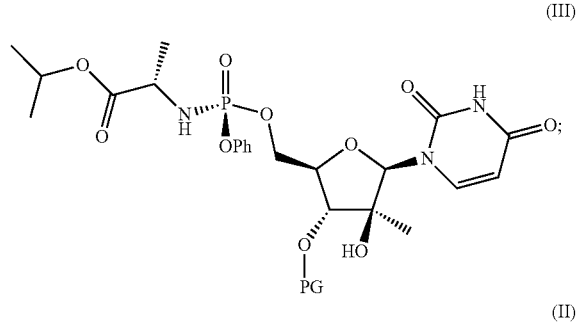

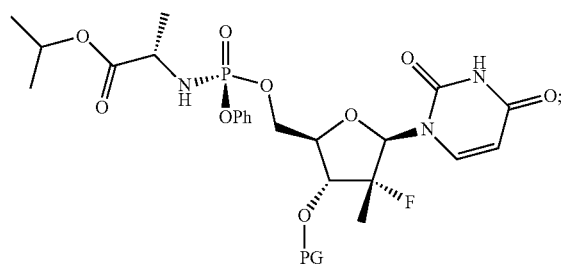

15 Claims, No Drawings

SYNTHESIS OF PHOSPHORAMIDATES

This application is a Section 371 national phase entry of PCT application PCT/EP2016/064370, filed Jun. 22, 2016. This application also claims the benefit of the earlier filing date of European patent application 15173155.1, filed Jun. 22, 2015.

The present invention relates to a novel and advantageous process for the preparation of phosphoramidates, in particular sofosbuvir. The novel process is characterized by a fluorination of a novel intermediate wherein, according to a particularly preferred process, an industrially compatible fluorination agent is employed.

Sofosbuvir according to the following formula

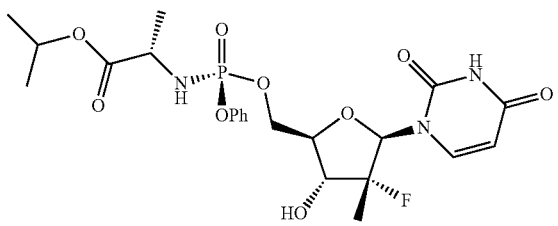 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

with IUPAC name (S)-isopropyl 2-(((S)-(((2R,3R,4R,5R)-5-(2,4-dioxo-3,4-dihydropyrimidin-1 (2H)-yl)-4-fluoro-3-hydroxy-4-methyltetrahydro furan-2-yl)methoxy)(phenoxy)phosphoryl)amino)propanoate is a drug inhibiting the RNA polymerase used by the hepatitis C virus to replicate its RNA.

The following route regarding the synthesis of sofosbuvir is disclosed in WO 2011/123645 A, WO 2008/121634 A, and WO 2010/135569 A:

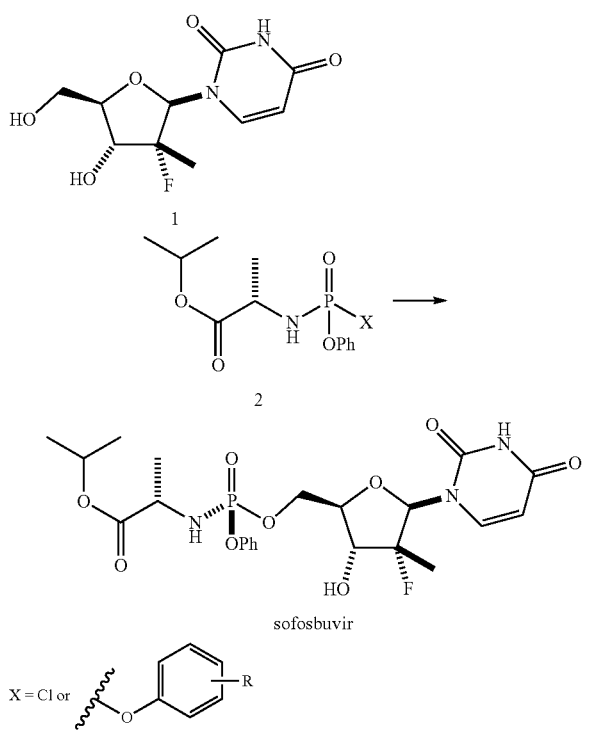

This route relies on the coupling of the fluorinated nucleoside derivative 1 with an activated phosphoramidate reagent 2. Building block 1 can be made via a variety of routes employing late- or early-stage fluorination. The benchmark route for 1 may appear to be an early-fluorination 10-step total synthesis as disclosed, for example, in WO 2006/031725 A and J. Org. Chem. 2009, 74, pp 6819. Building block 1 is also available commercially but is highly expensive. The coupling of 1 and 2 can be done non-diastereoselectively using 2 where X=Cl, and the two diastereomers of sofosbuvir are then separated by chromatographic methods or crystallization; reference is made, for example, to WO 2008/121634 A and WO 2010/135569 A. Alternatively, other activated phosphoramidates 2 can be used where X=substituted phenolates, as disclosed in WO 2011/123645 A, or other groups described in WO 2014/164533 A.

In view of the above, it is an object of the present invention to provide a process for preparing phosphoramidates, in particular for preparing sofosbuvir, wherein the use of the building block 1 is avoided. Surprisingly, it was found that such a process can be provided if a late-stage fluorination step is applied to a hitherto unknown intermediate.

Therefore, the present invention relates to a process for preparing a compound of formula (I)

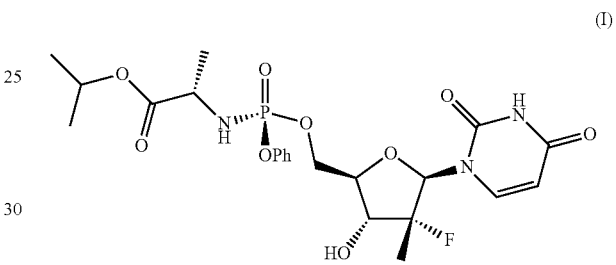

or a salt thereof, the process comprising
(i) providing a compound of formula (III)

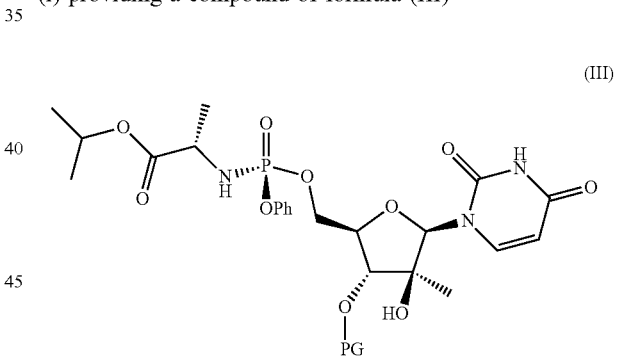

wherein PG is an inert electron withdrawing hydroxyl protecting group;
(ii) reacting the compound of formula (III) with a fluorinating agent, obtaining a compound of formula (II)

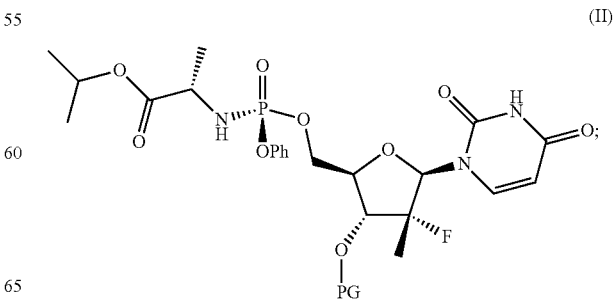

(iii) optionally isolating the compound of formula (II) from the reaction mixture obtained in (ii);

(iv) deprotecting the compound of formula (II) obtaining the compound of formula (I).

Surprisingly, it was found that the novel compound of formula (III) can be efficiently fluorinated without decomposition, epimerization or any other problems, despite the presence of a chiral phosphoramidate moiety. Without wanting to be bound by any theory, it is believed that one of the key features of the novel process of the invention is the use of the combination of the protecting group and the fluorination reagent. Further, the late-stage fluorination step reduces the amount of deoxyfluorinating reagent which is usually a cost driver for the industrial-scale production. Yet further, it was found that the diastereoselectivity and the chemical stability of the phosphoramidate moiety are not compromised in the fluorination.

In the context of the present invention, the term "inert" when used in the context of "inert electron withdrawing hydroxyl protecting group" refers to electron withdrawing hydroxyl protecting groups which do not react at the neighboring tertiary carbon of the furanose ring, such as in position 2'. In particular, these hydroxyl protecting groups do not engage in nucleophilic neighboring group participation by reacting at the tertiary carbon of the furanose ring, such as the tertiary carbon in position 2'. Regarding this lack of neighboring group participation, reference is made, for example, to Capon, B.; McManus, S. P.; *Neighbouring Group Participation*; Plenum: New York, 1976, page 11; and to Capon, B. Q. *Rev. Chem. Soc.* 1964, 18, pages 45-111, the respective content of which is incorporated herein be reference.

Preferably, the inert electron withdrawing hydroxyl protecting group PG is $C(O)CH_nX_{3-n}$ wherein X is halogen, preferably F, Cl, Br, I, and wherein n is 0, 1, or 2. More preferably, the inert electron withdrawing hydroxyl protecting group PG is $C(O)CH_nF_{3-n}$ with n being 0, 1, or 2. More preferably, the inert electron withdrawing hydroxyl protecting group PG is $C(O)CF_3$. Therefore, it is preferred that the compound of formula (III) is (III)

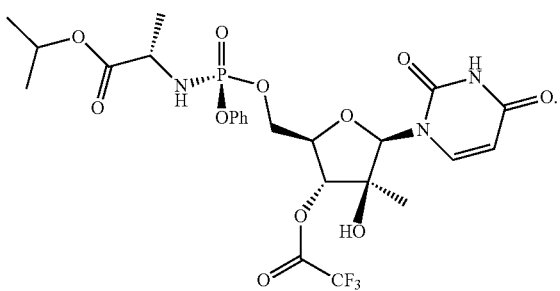

Also preferably, the inert electron withdrawing hydroxyl protecting group PG is $SO_2Z$ wherein Z is preferably Me (methyl), Ph (phenyl), p-Me-Ph (tosyl), $p-NO_2$-Ph (paranosyl), $o-NO_2$-Ph (ortho-nosyl), $o-CF_3$-Ph (ortho-trifluoromethylphenyl) or $CF_3$ (triflyl).

Also preferably, the inert electron withdrawing hydroxyl protecting group PG is a residue of formula (E)

(E)

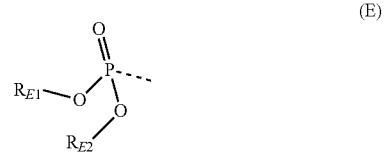

where the dotted line indicates the bond via which the residue is linked to the oxygen atom, wherein $R_{E1}$ and $R_{E2}$ are independently from each other alkyl or aryl, or, together, are a group $—(CH_2)_q—$ forming a ring together with the oxygen atoms to which $R_{E1}$ and $R_{E2}$ are bound and the P atom to which said oxygen atoms are bound, where q is preferably 2, 3, 4, 5, 6, or 7, more preferably 2, 3, 4, 5, or 6, more preferably 2, 3, 4, or 5, more preferably 2, 3, or 4. Preferably, $R_{E1}$ is $C_1$-$C_6$ alkyl, more preferably $C_1$-$C_4$ alkyl, more preferably $C_1$-$C_2$ alkyl, or aryl, more preferably phenyl or naphthyl. Preferably, $R_{E2}$ is $C_1$-$C_6$ alkyl, more preferably $C_1$-$C_4$ alkyl, more preferably $C_1$-$C_2$ alkyl, or $C_3$-$C_6$ cycloalkyl, more preferably $C_5$-$C_6$ cycloalkyl, or aryl, more preferably phenyl or naphthyl.

Also preferably, the inert electron withdrawing hydroxyl protecting group PG is $CH=CH_2—CO_2R_x$ or $C(O)—CH_2—CO_2R_x$ wherein $R_x$ is alkyl, or aryl, or cycloalkyl wherein $R_x$ is preferably $C_1$-$C_6$ alkyl, more preferably $C_1$-$C_4$ alkyl, more preferably $C_1$-$C_2$ alkyl, or $C_3$-$C_6$ cycloalkyl, more preferably $C_5$-$C_6$ cycloalkyl, or aryl, more preferably phenyl or naphthyl.

The fluorinating agent used according to (ii) preferably comprises one or more of (diethylamino)difluorosulfonium tetrafluoroborate and difluoro(morpholino)sulfonium tetrafluoroborate. More preferably, the fluorinating agent is one or more of (diethylamino)difluorosulfonium tetrafluoroborate and difluoro(morpholino)sulfonium tetrafluoroborate. More preferably, the fluorinating agent comprises, more preferably is, (diethylamino)difluorosulfonium tetrafluoroborate.

More preferably, the inert electron withdrawing hydroxyl protecting group PG is $C(O)CH_nX_{3-n}$, more preferably $C(O)CF_3$, and the fluorinating agent according to (ii) comprises, preferably is, (diethylamino)difluorosulfonium tetrafluoroborate.

Preferably, prior to the reacting according to (ii), the molar ratio of the fluorinating agent relative to the compound of formula (III) is in the range of from 0.1:1 to 3:1, more preferably in the range of from 0.5:1 to 2.7:1, more preferably in the range of from 1:1 to 2.3:1, more preferably in the range of from 1.25:1 to 2:1, more preferably in the range of from 1.45:1 to 1.65:1.

Preferably, according to (ii), the compound of formula (III) is reacted with the fluorinating agent in the presence of a fluorination promotor. With regard to the chemical nature of the fluorination promotor, no specific restrictions exist provided that the reaction according to (ii) can be carried out. Preferably, the fluorination promotor comprises, preferably is, one or more of triethylamine trihydrofluoride (TEA 3HF), triethylamine dihydrofluoride (TEA 2HF), and diazabicycloundec-7-ene (DBU), preferably one or more of triethylamine trihydrofluoride and triethylamine dihydrofluoride. More preferably, the fluorination promotor comprises, preferably is, one or more of triethylamine trihydrofluoride (TEA 3HF) and triethylamine dihydrofluoride (TEA 2HF). More preferably, the fluorination promotor comprises, preferably is, triethylamine dihydrofluoride (TEA 2HF).

Preferably, prior to the reacting according to (ii), the molar ratio of the fluorination promotor relative to the compound of formula (III) is in the range of from 0.1:1 to 3:1, more preferably in the range of 0.5:1 to 2.9:1, more preferably in the range of from 1:1 to 2.7:1, more preferably in the range of from 1.75:1 to 2.5:1, more preferably in the range of from 1.9:1 to 2.1:1, more preferably in the range of from 1.95:1 to 2.05:1.

Therefore, the present invention relates to the process as defined above, wherein the inert electron withdrawing hydroxyl protecting group PG is $C(O)CH_nX_{3-n}$, more preferably $C(O)CF_3$, the fluorinating agent according to (ii) comprises, preferably is, (diethylamino)difluorosulfonium tetrafluoroborate, and the reacting according to (ii) is carried out in the presence of a fluorination promotor which comprises, preferably is, one or more of triethylamine trihydrofluoride (TEA 3HF) and triethylamine dihydrofluoride (TEA 2HF), preferably triethylamine dihydrofluoride (TEA 2HF).

Preferably, according to (ii), the compound of formula (III) is reacted with the fluorinating agent in a solvent. Preferred solvents are organic solvents, more preferred are aprotic organic solvents. More preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane. More preferably, the solvent comprises, preferably is, one or more of dichloromethane, dichloroethane, chloroform, toluene, tetrahydrofuran, methyl tert-butyl ether, 1,4-dioxane, and nitromethane. More preferably, the solvent comprises, preferably is, one or more of dichloromethane and tetrahydrofuran. According to the present invention, the solvent used is preferably an anhydrous solvent. More preferably, the solvent comprises, preferably is, dichloromethane, preferably anhydrous dichloromethane.

Therefore, the present invention relates to the process as defined above, wherein the inert electron withdrawing hydroxyl protecting group PG is $C(O)CH_nX_{3-n}$, more preferably $C(O)CF_3$, the fluorinating agent according to (ii) comprises, preferably is, (diethylamino)difluorosulfonium tetrafluoroborate, the reacting according to (ii) is carried out in the presence of a fluorination promotor which comprises, preferably is, one or more of triethylamine trihydrofluoride (TEA 3HF) and triethylamine dihydrofluoride (TEA 2HF), preferably triethylamine dihydrofluoride (TEA 2HF), and the reacting according to (ii) is carried out in a solvent, preferably an aprotic organic solvent, more preferably dichloromethane.

With regard to the temperature at which the reacting according to (ii) is carried out, no specific restrictions exist. Among others, the temperature will depend on the chemical nature of the solvent if a solvent is used according to (ii). Preferably, according to (ii), the reacting is carried out at a temperature in the range of from 0 to 40° C., more preferably in the range of from 5 to 35° C., more preferably in the range of from 10 to 30° C., more preferably in the range of from 15 to 25° C., more preferably in the range of from 20 to 25° C.

With regard to the period of time for which the reacting according to (ii) is carried out, no specific restrictions exist. Preferably, according to (ii), the reacting is carried out for a period of time in the range of from 0.1 to 24 h, more preferably in the range of from 0.15 to 12 h, more preferably in the range of from 0.2 to 6 h, more preferably in the range of from 0.3 to 5 h, more preferably in the range of from 0.4 to 4 h, more preferably in the range of from 0.5 to 2 h.

It is conceivable that after (ii), the compound of formula (II) is isolated, preferably isolated from the reaction mixture obtained in (ii), in particular after the reaction according to (ii) is completed or essentially completed. While there are no specific restrictions regarding said isolation, it may be preferred the such an isolating step (iii) comprises
(iii.1) extracting the compound of formula (II) from the mixture obtained in (ii);
(iii.2) separating the compound of formula (II) from the mixture obtained in (iii.1).

Preferably, said isolating according to (iii) or said separating according to (iii.2) may comprise filtration, centrifugation, drying, or a combination of two or more thereof.

According to the present invention, it is especially preferred that after (ii) and before (iv), the compound of formula (II) is not isolated from the reaction mixture obtained in (ii). In particular, it is preferred especially preferred that the reaction mixture obtained in (ii) is used as starting mixture for the deprotecting according to (iv). This feature of the novel process according to which no isolation or purification is necessary after fluorination represents a further advantage of the novel process. Thus, the present invention relates to a process for preparing a compound of formula (I) or a salt thereof, the process comprising
(i) providing a compound of formula (III);
(ii) reacting the compound of formula (III) with a fluorinating agent, obtaining a compound of formula (II) obtaining a reaction mixture and using this reaction mixture as starting material in the subsequent step (iv);
(iv) deprotecting the compound of formula (II) obtaining the compound of formula (I).

With regard to the deprotecting according to (iv), no specific restrictions exist, provided that by this step, the compound of formula (I) is obtained. Preferably, the deprotecting according to (iv) comprises
(iv.1) reacting the compound of formula (II) with an aqueous system, obtaining the compound of formula (I).

A preferred aqueous system according to the invention essentially consists of water. The term "essentially consisting of" as used in this context if the present application relates to an aqueous system which consists of water, preferably de-ionized (DI) water which only contains unavoidable impurities. More preferably, the aqueous system comprises, preferably essentially consists of, water and an acid, preferably an inorganic acid. Preferably, at least 99 weight %, more preferably at least 99.5 weight-%, more preferably at least 99.9 weight-% of the aqueous system consist of water and optionally the acid. Preferred acids include, but are not limited to, HCl, $H_2SO_4$, $HNO_3$, $NH_4Cl$, HCOOH, HOAc, or a buffer system having a pH in the range of from 4 to 7. More preferably, the acid, more preferably the inorganic acid, comprises, more preferably is, HCl. Such preferred aqueous systems preferably have a pH in the range of from 0 to 6, more preferably in the range of from 1 to 6, more preferably in the range of from 1 to 5, more preferably in the range of from 1 to 4, more preferably in the range of from to 3, more preferably in the range of from 1 to 2, as determined using a pH sensitive glass electrode.

Here, a further advantage of the novel process manifests. In particular with regard to the preferred hydroxyl protecting group $C(O)CF_3$, it is noted that this protecting group, as soon as the fluorination product, the compound of formula (II), is exposed to water, the compound is spontaneously deprotected giving directly sofosbuvir, and the protecting group is "traceless".

With regard to the temperature at which the reacting according to (ii) is carried out, no specific restrictions exist.

Preferably, the reacting according to (iv.1) is carried out at a temperature in the range of from 0 to 40° C., more preferably in the range of from 5 to 35° C., more preferably in the range of from 10 to 35° C., more preferably in the range of from 15 to 30° C., more preferably in the range of from 20 to 30° C.

Since it is preferred, as mentioned above, that the reacting according to (ii) is carried out in the presence of a solvent, and since it is further preferred that step (iv) is carried out directly after step (ii), it is also preferred that the compound of formula (I), obtained from the deprotecting according to (iv), is obtained in the solvent preferably employed according to (ii). Yet further, since the deprotecting according to (iv) is preferably carried out using an aqueous system, a reaction mixture is obtained from (iv) comprising an organic phase and an aqueous phase wherein the organic phase comprises the compound of formula (I) is comprised in the organic phase. While it may be conceivable to use this reaction mixture for specific purposes, it is especially preferred to suitably separate the compound of formula (I) from this reaction mixture. Therefore, it is preferred that the process of the invention comprises (iv.2) working up the reaction mixture obtained in (iv.1), obtaining the compound of formula (I).

No specific restrictions exist regarding said working-up of the reaction mixture. It is preferred that the organic phase mentioned above is separated from the aqueous phase mentioned above, wherein it is further preferred that the organic phase is subjected to drying wherein the organic solvent is suitably removed. Suitable drying methods include, but are not limited to, evaporation, such as evaporation under reduced pressure. From said drying, the compound of formula (I) is obtained in dried form. It is also possible that the aqueous phase obtained from said separating may comprise a minor amount of the compound of formula (I). In this case, it is preferred that the aqueous phase is subjected to a washing step with a suitable organic solvent. Preferred solvents used for this washing include, but are not limited to, the preferred solvents described hereinabove as the solvents preferably employed according to (ii). More preferably, the solvent used as for this washing is the solvent used preferably used according to (ii). The organic phase or phases obtained from this washing is preferably subjected to drying wherein the organic solvent is suitably removed. Suitable drying methods include, but are not limited to, evaporation, such as evaporation under reduced pressure. From said drying, the compound of formula (I) is obtained in dried form. Therefore, the present invention relates to the process as discussed above, wherein the working up according to (iv.2) comprises (iv.2.1) separating the organic phase from the aqueous phase;
(iv.2.2) optionally washing the aqueous phase with an organic solvent, preferably a solvent as defined in any one of embodiments 23 to 25, preferably 24 or 25, more preferably 25;
(iv.2.3) optionally drying the organic phase obtained in (iv.2.1), and optionally the organic phase obtained in (iv.2.2), obtaining the compound of formula (I).

Preferably, after (iv), the compound of formula (I) is further purified. Such purification may include, for example, purification by chromatography and/or crystallization. Therefore, the present invention relates to the process as described above, comprising (v) purifying the compound of formula (I);
wherein the purifying according to (v) preferably comprises
(v.1) crystallizing the compound of formula (I), obtaining the compound of formula (I) in its mother liquor, preferably from a solvent comprising one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably dichloromethane;
(v.2) preferably separating the crystallized compound of formula (I) from its mother liquor, obtaining the compound of formula (I) in crystalline form, said separating preferably comprising
(v.2.1) subjecting the mother liquor comprising the crystallized compound of formula (I) to filtration, obtaining a filter cake comprising the compound of formula (I);
(v.2.2) optionally washing the filter cake comprising the compound of formula (I), preferably using a washing agent comprising one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably dichloromethane;
(v.2.3) drying the optionally washed filter cake, obtaining the compound of formula (I).

Step (i)

Preferably, the providing of the compound of formula (III) according to (i) comprises
(i.1) providing a compound of formula (IV)

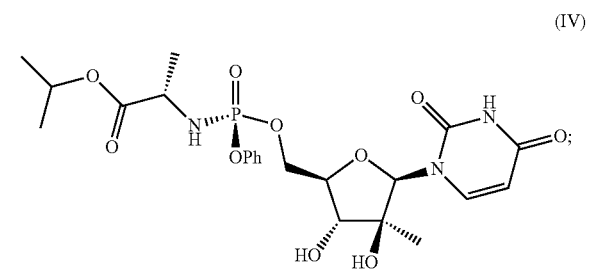 [SMILES: CC(C)OC(=O)[C@H](C)N[P@](=O)(OC[C@H]1O[C@@H](n2ccc(=O)[nH]c2=O)[C@@](C)(O)[C@@H]1O)Oc1ccccc1]

(i.2) reacting the compound of formula (IV) with a hydroxyl protecting agent Y-PG, obtaining the compound of formula (III).

After step (i.2), the compound of formula (III) can be optionally purified in a step (i.3).

With regard to the hydroxyl protecting agent Y-PG according to (i.2), no specific restrictions exist provided that the compound of formula (III) is obtained. Preferably, in the hydroxyl protecting agent Y-PG, Y is a halide such as F, Cl, Br, I, preferably Cl. Therefore, preferred hydroxyl protecting agents are, for example, $ClC(O)CCl_3$, $ClC(O)CF_3$, $ClC(O)CH_2Cl$, $Cl_2HCC(O)Cl$, $F_2HCC(O)$—Cl, $FH_2CC(O)$—Cl or Cl—$SO_2$Me. Preferred hydroxyl protecting agents Y-PG are also acid anhydrides, and specifically preferred hydroxyl protecting agents Y-PG are, for example, $O(C(O)CF_3)_2$ or $O(C(O)CH_2Cl)_2$. More preferably, the hydroxyl protecting agent Y-PG is ClC(O)CCl₃, O(C(O)CF₃)₂ or O(C(O)CH₂Cl)₂. More preferably, the hydroxyl protecting agent Y-PG is trifluoroacetic anhydride.

Preferably, prior to the reacting according to (i.2), the molar ratio of the hydroxyl protecting agent Y-PG relative to the compound of formula (IV) is in the range of from 1:1 to 3:1, preferably in the range of from 1.01:1 to 2:1, more preferably in the range of from 1.02:1 to 1.5:1.

Preferably, according to (i.2), the compound of formula (IV) is reacted with the hydroxyl protecting agent Y-PG in a solvent. Preferred solvents are organic solvents, more preferred are aprotic organic solvents. More preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane. More preferably, the solvent comprises, preferably is, one or more of dichloromethane, dichloroethane, chloroform, toluene, tetrahydrofuran, methyl tert-butyl ether, 1,4-dioxane, and nitromethane. More preferably, the solvent comprises, preferably is, one or more of dichloromethane and tetrahydrofuran. According to the present invention, the solvent used is preferably an anhydrous solvent. More preferably, the solvent comprises, preferably is, dichloromethane, preferably anhydrous dichloromethane. More preferably, the solvent preferably used according to (ii) is used according to (i.2).

With regard to the temperature at which the reacting according to (i.2) is carried out, no specific restrictions exist. Among others, the temperature will depend on the chemical nature of the solvent if a solvent is used according to (i.2). Preferably, according to (i.2), the reacting is carried out at a temperature in the range of from 0 to 40° C., more preferably in the range of from 5 to 35° C., more preferably in the range of from 10 to 30° C., more preferably in the range of from 15 to 25° C., more preferably in the range of from 20 to 25° C.

With regard to the period of time for which the reacting according to (i.2) is carried out, no specific restrictions exist. Preferably, according to (i.2), the reacting is carried out for a period of time in the range of from 0.1 to 24 h, preferably in the range of from 0.2 to 6 h, more preferably in the range of from 0.5 to 3 h.

It is conceivable that after (i.2), the compound of formula (III) is purified in a step (i.3), preferably including, for example, separating the compound of formula (III) from the reaction mixture obtained in (i.2), in particular after the reaction according to (i.2) is completed or essentially completed. Preferably, said separating according to (i.3) may comprise filtration, centrifugation, drying, or a combination of two or more thereof. Further, it may be preferred that the purifying according to (i.3) comprises crystallization of the compound of formula (III).

According to the present invention, it is especially preferred that after (i.2), in particular after (i.2) and prior to (ii), the compound of formula (III) is not purified. In this preferred feature, a further major advantage of the novel process manifests in that the above-discussed "traceless" protecting group strategy requires no purification after protection and, as already discussed above, eliminates an extra synthetic step of deprotection. Therefore, it is preferred that the reaction mixture obtained from (i.2) is directly employed in (ii).

Further, the present invention relates to the compound of formula (III), obtainable or obtained by the process as described above.

Step (i.1)

Preferably, the providing of the compound of formula (IV) according to (i.1) comprises (i.1.1) reacting a compound of formula (V)

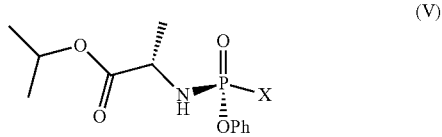

(V)

with a compound of formula (VI)

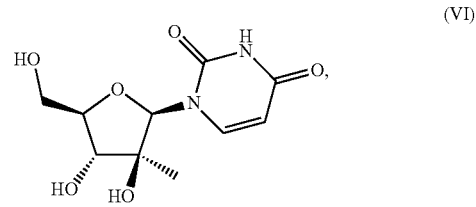 [SMILES: C[C@]1(O)[C@H](O)[C@@H](CO)O[C@H]1n1ccc(=O)[nH]c1=O]

(VI)

obtaining the compound of formula (IV).

After step (i.1.1), the compound of formula (IV) can be optionally purified in a step (i.1.2). According to the present invention, it is preferred that compound of formula (IV) is purified in a step (i.1.2).

Thus, the novel process of the invention is in particular characterized in that, starting from the two building blocks of formula (V) and formula (VI), only 2 purification steps are needed.

Preferably, the residue X of the compound of formula (V) according to (i.1.1) is a leaving group which is suitable for a nucleophilic substitution reaction. No specific limitations with regard to the chemical nature of the leaving group X exist, provided that the compound of formula (IV) is obtained.

A preferred leaving group —X is —(Z—)$_n$R$_Y$ where n is 0 or 1 and Z is O, N or S. With regard to this leaving group, it is preferred, for example, that n is 1 and R$_Y$ is alkyl, aryl, or heteroaryl, each optionally substituted with one or more electron withdrawing groups, preferably aryl optionally substituted with one or more electron withdrawing groups, more preferably phenyl optionally substituted with one or more electron withdrawing groups, wherein the one or more electron withdrawing groups are preferably F, Cl, Br, I, or NO$_2$. It is also preferred that n is 1 and R$_Y$ is a residue of formula (A)

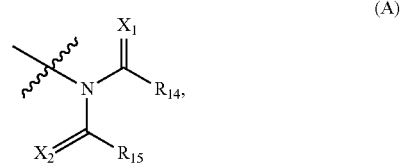

(A)

a residue of formula (B)

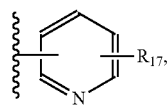

a residue of formula (C)

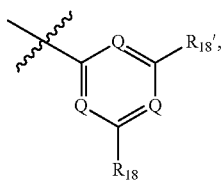

or a residue of formula (D)

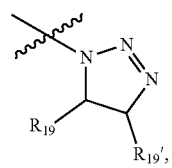

wherein at each occurrence
$X_1$ and $X_2$ are independently O or S;
$R_{14}$ and $R_{15}$ are independently H, OH, $NH_2$, $C_1$-$C_6$ alkyl or $C_1$-$C_6$ alkoxy, or
$R_{14}$ and $R_{15}$, together with the structure —C—N—C— according to formula (A), form an optionally substituted, 5-, 6-, or 7-membered saturated or partially unsaturated ring, wherein said ring is optionally fused to a 5- or 6-membered, optionally substituted ring which is a $C_5$-$C_6$ cycloalkyl, an aryl or a heterocycle comprising one or more heteroatoms independently being N, O or S;
$R_{17}$ is an electron-withdrawing group, preferably F, Cl, Br, I, $NO_2$, CHO, C(O)OH, C(O)—($C_1$-$C_6$)alkyl, CN, or C(O)Cl;
$R_{18}$ and $R_{18'}$ are independently F, Cl, Br, I, or $C_1$-$C_6$ alkoxy;
each Q is independently C or N, wherein at least one Q is N;
$R_{19}$ and $R_{19'}$ are independently H, OH, $NH_2$, $C_1$-$C_6$ alkyl optionally substituted with at least one of OH and $NH_2$, or $C_1$-$C_6$ alkoxy optionally substituted with at least one of OH and $NH_2$; or
$R_{19}$ and $R_{19'}$ taken together form an optionally substituted 5-, 6-, or 7-membered saturated or partially unsaturated or aromatic ring, wherein the ring is optionally fused to a 5- or 6-membered, optionally substituted ring which is a $C_5$-$C_6$ cycloalkyl, an aryl, preferably benzo, or a heterocycle comprising one or more heteroatoms independently being N, O or S, the 5- or 6-membered optionally substituted ring preferably being heteroaryl;
$R_{20}$, $R_{21}$, $R_{22}$ and $R_{23}$ are each independently H, aryl, or $C_1$-$C_6$ alkyl optionally substituted with at least one of $C_1$-$C_6$ alkoxy optionally substituted with at least one of OH and $NH_2$, or
$R_{20}$ and $R_{22}$, or $R_{20}$ and $R_{23}$, or $R_{21}$ and $R_{22}$, or $R_{21}$ and $R_{23}$ when taken together form an optionally substituted 5-, 6-, or 7-membered saturated or partially unsaturated or aromatic ring which is an aryl, preferably benzo, or a heterocycle comprising one or more heteroatoms independently being N, O or S, the 5-, 6-, or 7-membered saturated or partially unsaturated or aromatic ring preferably being heteroaryl. More preferably, n is 1 and $R_Y$ is a residue of formula (A)

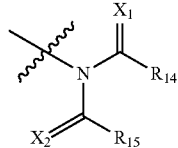

wherein
$X_1$ and $X_2$ are independently O or S;
$R_{14}$ and $R_{15}$ are independently H, OH, $NH_2$, $C_1$-$C_6$ alkyl or $C_1$-$C_6$ alkoxy, or
$R_{14}$ and $R_{15}$, together with the structure —C—N—C— according to formula (A), form an optionally substituted, 5-, 6-, or 7-membered saturated or partially unsaturated ring, wherein said ring is optionally fused to a 5- or 6-membered, optionally substituted ring which is a $C_5$-$C_6$ cycloalkyl, an aryl or a heterocycle comprising one or more heteroatoms independently being N, O or S,
wherein $R_Y$ is preferably a residue of formula (Ab)

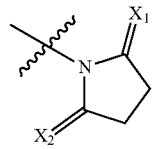

or a residue of formula (Ac)

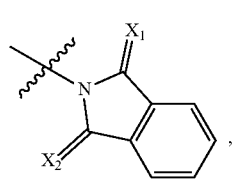

wherein $X_1$ is preferably O and $X_2$ is preferably O. It is also possible that n is 0 and $R_Y$ is a residue of formula (A1)

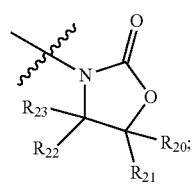

wherein at each occurrence
$R_{20}$, $R_{21}$, $R_{22}$ and $R_{23}$ are each independently H, aryl, or $C_1$-$C_6$ alkyl optionally substituted with at least one of $C_1$-$C_6$ alkoxy optionally substituted with at least one of OH and NH$_2$; or R$_{20}$ and R$_{22}$, or R$_{20}$ and R$_{23}$, or R$_{21}$ and R$_{22}$, or R$_{21}$ and R$_{23}$ when taken together form an optionally substituted 5-, 6-, or 7-membered saturated or partially unsaturated or aromatic ring which is an aryl, preferably benzo, or a heterocycle comprising one or more heteroatoms independently being N, O or S, the 5-, 6-, or 7-membered saturated or partially unsaturated or aromatic ring preferably being heteroaryl.

Another preferred leaving group —X is —Cl.

In particular with regard to the above-mentioned preferred leaving groups X, the compound of formula (V) is reacted with the compound of formula (VI) in the presence of a Lewis acid. No specific restrictions exist with regard to the chemical nature of the Lewis acid employed in a). Preferably, the Lewis acid comprises a twice positively charged ion or a three times positively charged ion, more preferably a twice positively charged metal ion or a three times positively charged metal ion. Generally, it is also conceivable that the Lewis acid comprises a twice positively charged ion and a three times positively charged ion, preferably a twice positively charged metal ion and a three times positively charged metal ion. With regard to the twice positively charged ion, it is preferred that it comprises, more preferably is, a Zn ion, a Mg ion, a Cu ion, or an Fe ion. More preferably, the twice positively charged ion comprises, more preferably is, a Zn ion or a Mg ion. More preferably, the twice positively charged ion comprises, more preferably is, a Zn ion. With regard to the three times positively charged ion, it is preferred that it comprises, more preferably is, a Mn ion. Regarding the Lewis acid comprising a twice positively charged ion comprising, more preferably being, a Zn ion, no specific restrictions exist. Preferred Lewis acids comprise, more preferably are, Zn halides. More preferably, the Lewis acid comprises, preferably is, one or more of ZnBr$_2$, ZnCl$_2$, and ZnI$_2$. More preferably, the Lewis acid comprises, preferably is, ZnBr$_2$. It is also conceivable that the Lewis acid is one or more of ZnBr$_2$, ZnCl$_2$, ZnI$_2$, MgBr$_2$, MgBr$_2$.OEt$_2$, CuCl$_2$, Cu(acetylacetonate)$_2$, and Fe(II) fumarate. Regarding the Lewis acid comprising a three times positively charged ion comprising, more preferably being, a Mn ion, no specific restrictions exist. Preferred Lewis acids comprise, more preferably are, Mn(acetylacetonate)$_3$.

Regarding the amount of the Lewis acid relative to the amount of the compound of formula (VI) employed in (i.1.1), no specific restrictions exist. Preferably, prior to the reaction according to (i.1.1), the molar ratio of the Lewis acid relative to the compound of formula (VI) is in the range of from 0.1:1 to 5:1. More preferably, prior to the reaction according to (i.1.1), the molar ratio of the Lewis acid relative to the compound of formula (VI) is in the range of from 0.2:1 to 5:1, preferably in the range of from 0.5:1 to 3:1, more preferably in the range of from 0.75:1 to 1.5:1.

Preferably, according to (i.1.1), the compound of formula (V) is reacted with the compound of formula (VI) in the presence of a base, preferably an organic base, more preferably an organic nitrogenous base. More preferably, the organic base comprises one or more of an amine, an amidine, and a heteroaromatic compound comprising a basic ring-nitrogen atom, preferably one or more of ethyldiisopropylamine, triethylamine, diethylamine, 1,8-diazabicycloundec-7-ene, pyridine, quinoline, isoquinoline, acridine, pyrazine, imidazole, benzimidazole, and pyrazole. More preferably, the organic base comprises, preferably is, triethylamine.

Regarding the amount of the base relative to the amount of the compound of formula (VI) employed in (i.1.1), no specific restrictions exist. Preferably, prior to the reaction according to (i.1.1), the molar ratio of the base relative to the compound of formula (VI) is in the range of from 0.1:1 to 5:1. More preferably, prior to the reaction according to (i.1.1), the molar ratio of the base relative to the compound of formula (VI) is in the range of from 1:1 to 5:1, more preferably in the range of from 2:1 to 5:1, more preferably in the range of from 2.5:1 to 4:1, more preferably in the range of from 2.5:1 to 3.5:1.

Generally, it may be conceivable that the reacting according to (i.1.1) is carried out in the presence of a Lewis acid and in the absence of said base. Generally, it may also be conceivable that the reacting according to (i.1.1) is carried out in the presence of a base and in the absence of said Lewis acid. Preferably, the reacting according to (i.1.1) is carried out in the presence of said Lewis acid and in the presence of said base.

Preferably, prior to the reacting according to (i.1.1), the molar ratio of the compound of formula (V) relative to the compound of formula (VI) is in the range of from 0.5:1 to 5:1, preferably in the range of from 0.8:1 to 2:1, more preferably in the range of from 0.9:1 to 1.2:1.

Preferably, according to (i.1.1), the compound of formula (V) is reacted with the compound of formula (VI) in a solvent. Preferred solvents are organic solvents, more preferred are aprotic organic solvents. More preferably, the solvent comprises, preferably is, one or more of methylene chloride, methyl tert-butyl ether, tetrahydrofuran, dimethylsulphoxide, and dimethylformamide. More preferably, the solvent comprises, preferably is, tetrahydrofuran.

With regard to the temperature at which the reacting according to (i.1.1) is carried out, no specific restrictions exist. Among others, the temperature will depend on the chemical nature of the solvent if a solvent is used according to (i.1.1). Preferably, according to (i.1.1), the reacting is carried out at a temperature in the range of from 0 to 80° C., more preferably in the range of from 0 to 50° C., more preferably in the range of from 0 to 25° C., more preferably in the range of from 0 to 20° C., more preferably in the range of from 0 to 15° C., more preferably in the range of from 0 to 10° C., more preferably in the range of from 0 to 5° C.

With regard to the period of time for which the reacting according to (i.1.1) is carried out, no specific restrictions exist. Preferably, according to (i.1.1), the reacting is carried out for a period of time in the range of from 0.5 to 48 h, preferably in the range of from 1 to 36 h, more preferably in the range of from 2 to 24 h.

As mentioned above, it is preferred that after (i.1.1), the compound of formula (IV) obtained from the reacting of the compound of formula (V) with the compound of formula (VI) is suitably purified. Preferably, said purifying comprises working up the reaction mixture obtained in (i.1.1), in particular after the reaction according to (i.1.1) is completed or essentially completed. While there are no specific restrictions regarding to said working up, it is preferred that it comprises (i.1.2.1) subjecting the reaction mixture obtained from (i.1.1) to solid-liquid separation;
(i.1.2.2) drying the preferably washed solid, obtaining a purified compound of formula (IV).

Regarding the solid-liquid separation according to (i.1.2.1), no specific limitations exist. Preferably, the solid-liquid separation comprises filtration. Preferably, after the separation, the separated solid phase is suitably washed. Preferred washing agents include, but are not limited to, organic solvents, preferably aprotic organic solvents. More preferably, the washing agent is one or more of methylene chloride, methyl tert-butyl ether, tetrahydrofuran, dimethylsulphoxide, and dimethylformamide.

Generally, it is conceivable that the separated and preferably washed solid is used as starting material for (ii.2). Preferably, the separated and preferably washed solid is subjected to further purification. While there are no specific restrictions regarding this further purification, it can be preferred that it comprises the following sequence of steps:

(i.1.2.3) dissolving the solid obtained from (i.1.2.2) in a solvent, preferably comprising one or more of dichloromethane, dichloroethane, chloroform, toluene, methyl ethyl ketone, ethyl acetate, butyl acetate, and nitromethane, preferably one or more of dichloromethane, toluene, ethyl acetate, butyl acetate and isopropyl acetate, more preferably comprising, preferably being, isopropyl acetate;

(i.1.2.4) admixing the solution obtained from (i.1.2.3) with an acidic aqueous system preferably comprising an acid which preferably comprises one or more of HCl, H₂SO₄, HNO₃, NH₄Cl, HCOOH, HOAc, said acid more preferably comprising, more preferably being, HCl;

(i.1.2.5) separating the aqueous phase from the organic phase;

(i.1.2.6) preferably extracting the aqueous phase, preferably with a solvent as defined in (i.1.2.3), more preferably with the solvent as defined in (i.1.2.3);

(i.1.2.7) drying the organic phases obtained from (i.1.2.5) and preferably (i.1.2.6), obtaining a purified compound of formula (IV);

(i.1.2.8) preferably further purifying the purified compound of formula (IV) obtained from (i.1.2.2), preferably from (i.1.2.7), wherein the further purifying preferably comprises column chromatography, more preferably silica gel column chromatography.

Further, the present invention relates to the compound of formula (IV), obtainable or obtained by the process as described above.

Hence, a preferred process of the present invention is a process for preparing a compound of formula (I)

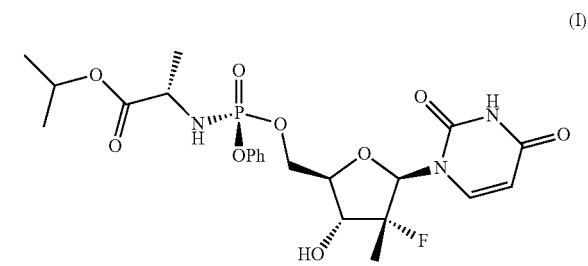 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

(I)

or a salt thereof, the process comprising
(i) providing a compound of formula (III)

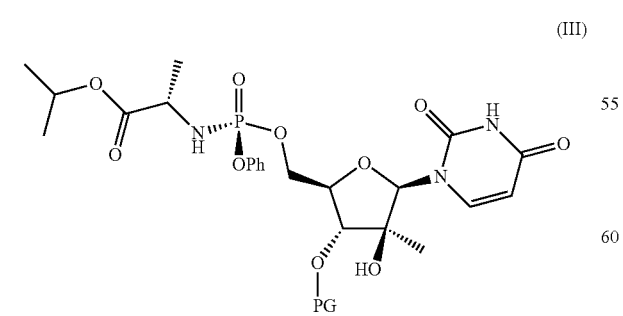

(III)

wherein PG is an inert electron withdrawing hydroxyl protecting group; wherein providing of the compound of formula (III) according to (i) comprises (i.1) providing a compound of formula (IV)

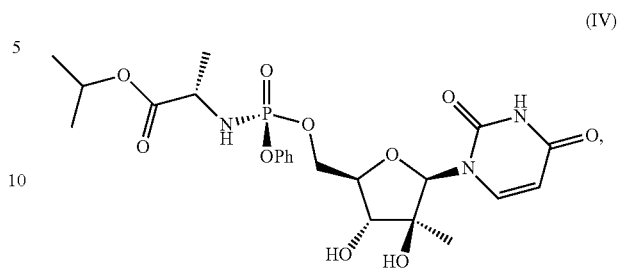

(IV)

wherein providing the compound of formula (IV) comprises
(i.1.1) reacting a compound of formula (V)

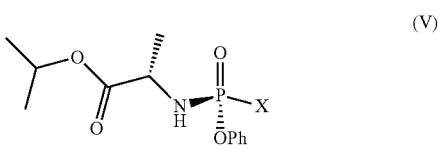

(V)

with a compound of formula (VI)

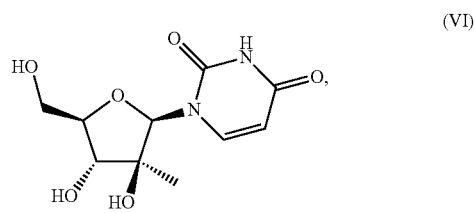

(VI)

wherein X is a leaving group which is suitable for a nucleophilic substitution reaction, obtaining the compound of formula (IV);

(i.1.2) purifying the compound of formula (IV);

(i.2) reacting the compound of formula (IV) with a hydroxyl protecting agent Y-PG, obtaining the compound of formula (III);

(ii) reacting the compound of formula (III) with a fluorinating agent, obtaining a compound of formula (II)

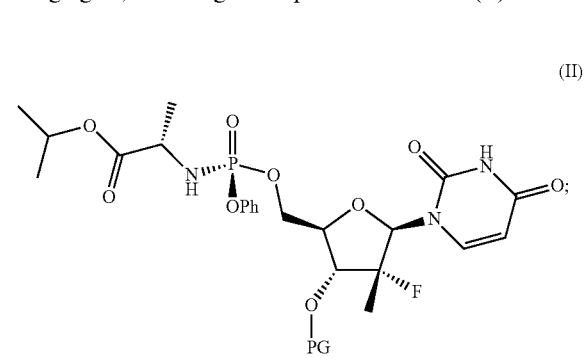

(II)

(iv) deprotecting the compound of formula (II) obtaining the compound of formula (I);

(v) purifying the compound of formula (I).

Further, a more preferred process of the present invention is a process for preparing a compound of formula (I)

(I)

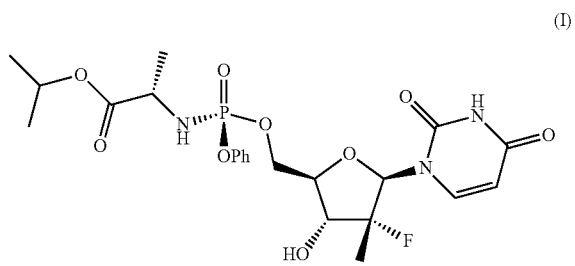 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

or a salt thereof, the process comprising
(i) providing a compound of formula (III)

(III)

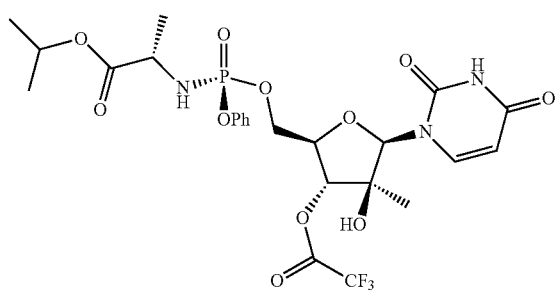

wherein providing of the compound of formula (III) according to (i) comprises
(i.1) providing a compound of formula (IV)

(IV)

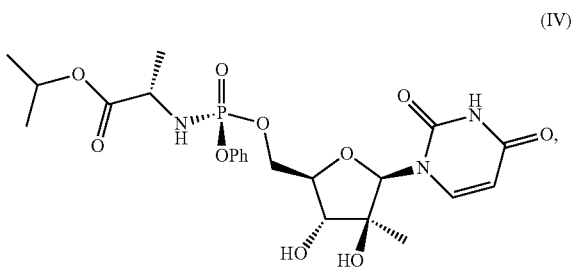 [SMILES: CC(C)OC(=O)[C@H](C)N[P@](=O)(OC[C@H]1O[C@@H](n2ccc(=O)[nH]c2=O)[C@@](C)(O)[C@@H]1O)Oc1ccccc1]

wherein providing the compound of formula (IV) comprises
(i.1.1) reacting a compound of formula (V)

(V)

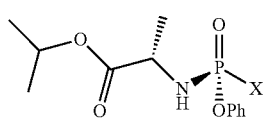

with a compound of formula (VI)

(VI)

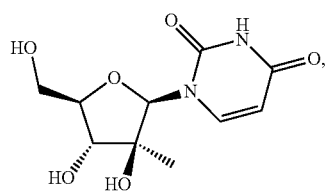

preferably in the presence of a Lewis acid and a base, wherein X is preferably as defined above, obtaining the compound of formula (IV);
(i.1.2) purifying the compound of formula (IV);

(i.2) reacting the compound of formula (IV) with a suitable hydroxyl protecting agent, preferably trifluoroacetic acid anhydride, obtaining the compound of formula (III);
(ii) reacting the compound of formula (III) with a fluorinating agent comprising one or more of (diethylamino)difluorosulfonium tetrafluoroborate and difluoro(morpholino)sulfonium tetrafluoroborate, obtaining a compound of formula (II)

(II)

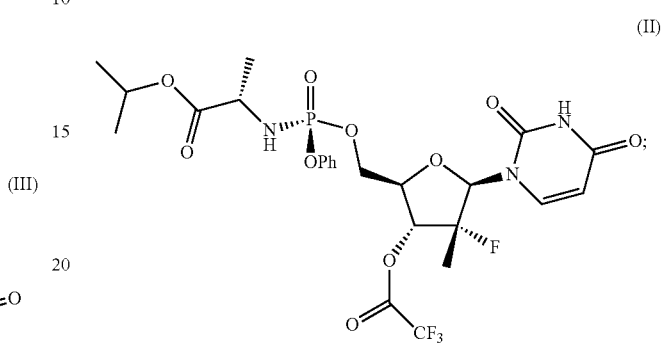

(iv) deprotecting the compound of formula (II) obtaining the compound of formula (I);
(v) purifying the compound of formula (I).

Summarized, the present invention relates to a novel process for preparing sofosbuvir based one, preferably two novel intermediates. A preferred process is characterized in a diastereoselective phosphoramidation of a non-fluorinated building block, the compound of formula (VI), followed specific protection of the 3'-OH group, preferably making use of the protecting group C(O)CF$_3$, and subsequent deoxyfluorination. When the respectively obtained reaction mixture is exposed to an aqueous system, 3'-OH deprotection occurs spontaneously. Thus, according to a preferred process and starting from the readily available compound of formula (VI), only 3 chemical (+1 spontaneous) steps and 2 purification steps are needed to prepare the compound of formal (I) wherein the diastereoselectivity and chemical stability of the phosphoramidate moiety are not compromised in the fluorination.

Compound of Formula (III)

As mentioned above, during the novel process of the invention, the compound (III) is obtained as intermediate. This hydroxyl-protected compound allows the deoxyfluorination from which the protected form of the compound of formula (I), the compound of formula (II), is obtained which in turn allows the simple and robust deprotection using an aqueous system, making a purification of the compound of formula (III) superfluous. Therefore, the compound of formula (III) is a key component of the novel process, and the present invention also relates to a compound of formula (III)

(III)

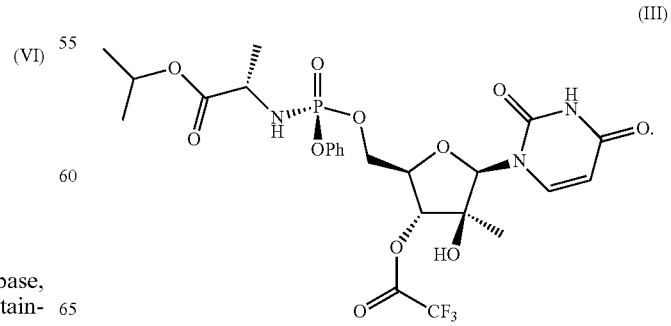

In particular, the present invention provides an advantageous mixture comprising the compound of formula (III), which mixture is the preferred starting material for the reacting according to (ii) and, thus, a key mixture of the novel process. Therefore, the present invention also relates to a mixture comprising the compound of formula (III) and a solvent, preferably an organic solvent, more preferably an aprotic organic solvent, wherein more preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran, wherein more preferably, the solvent comprises, preferably is, dichloromethane, preferably anhydrous dichloromethane. More preferably, this mixture further comprises a fluorinating agent which preferably comprises, more preferably is, one or more of (diethylamino)difluorosulfonium tetrafluoroborate and difluoro(morpholino)sulfonium tetrafluoroborate. More preferably, this mixture further comprises, in addition to the fluorinating agent, a fluorination promotor which preferably comprises, more preferably is, one or more of triethylamine trihydrofluoride (TEA 3HF), triethylamine dihydrofluoride (TEA 2HF), and diazabicycloundec-7-ene (DBU), preferably one or more of triethylamine trihydrofluoride and triethylamine dihydrofluoride. Consequently, the present invention also relates to the use of this mixture for preparing a compound of formula (II) or for preparing a compound of formula (I).

Compound of Formula (IV)

As mentioned above, during the novel process of the invention, the compound (IV) is preferably obtained as intermediate. This compound represents the very compound from which the protected compound of formula (III) from which, in turn, the protected form of the compound of formula (I), the compound of formula (II), is obtained which in turn allows the simple and robust deprotection using an aqueous system, making a purification of the compound of formula (III) superfluous. Therefore, also the compound of formula (IV) is a preferred key component of the novel process, and the present invention also relates to a compound of formula (IV)

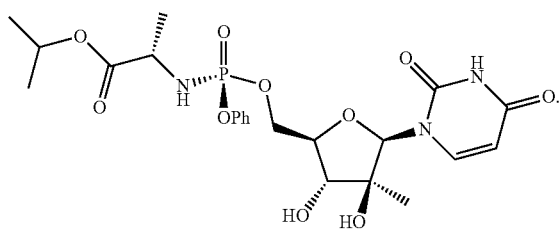

(IV)

In particular, the present invention provides an advantageous mixture comprising the compound of formula (IV), which mixture is the preferred starting material for the reacting according to (i.1.1) and, thus, a key mixture of the novel process. Therefore, the present invention also relates to a mixture comprising the compound of formula (IV) and a solvent, preferably an organic solvent, more preferably an aprotic organic solvent, wherein more preferably, the solvent comprises, preferably is, one or more of methylene chloride, methyl tert-butyl ether, tetrahydrofuran, dimethylsulphoxide, and dimethylformamide, wherein more preferably, wherein more preferably, the solvent comprises, preferably is, tetrahydrofuran. More preferably, this mixture further comprises a hydroxyl group protecting agent, preferably Y—C(O)CF$_3$, more preferably trifluoroacetic anhydride. Consequently, the present invention also relates to the use of this mixture for preparing a compound of formula (III) or for preparing a compound of formula (II) or for preparing a compound of formula (I).

Mixture Comprising the Compound of Formula (II)

As mentioned above, a mixture is obtained from reacting the compound of formula (III) with a fluorinating agent, which mixture comprises the hydroxyl-protected and deoxyfluorinated compound of formula (II). This mixture is preferably used without any purification or separation or isolation as the starting material for the deprotecting according to process step (iv). Thus, this mixture represents a key mixture of novel process, and thus, the present invention also relates to a mixture comprising a compound of formula (II)

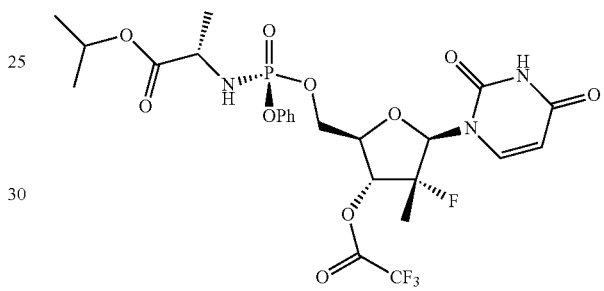

(II)

and a solvent, preferably an organic solvent, more preferably an aprotic organic solvent, wherein more preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran, wherein more preferably, the solvent comprises, preferably is, dichloromethane, preferably anhydrous dichloromethane. Consequently, the present invention also relates to the use of this mixture for preparing a compound of formula (I).

Mixture Comprising the Compounds of Formula (V) and Formula (VI)

The novel compound of formula (IV), discussed above and representing a preferred component of the novel process, is preferably prepared according step (i.1.1) which in turn is based on a specific starting mixture. This specific starting mixture comprises the compounds of formula (V) and formula (VI). Therefore, the present invention also relates to a mixture comprising a compound of formula (V) and a compound of formula (VI). Preferably, this mixture further comprises a solvent, preferably an organic solvent, more preferably an aprotic organic solvent, wherein more preferably, the solvent comprises, preferably is, one or more of methylene chloride, methyl tert-butyl ether, tetrahydrofuran, dimethylsulphoxide, and dimethylformamide, wherein more preferably, wherein more preferably, the solvent comprises, preferably is, tetrahydrofuran. More preferably, this mixture further comprises a Lewis acid and/or a base, preferably a Lewis acid and a base, wherein the Lewis acid preferably comprises a twice positively charged ion or a three times positively charged ion, more preferably a twice positively charged metal ion or a three times positively charged metal ion, wherein the twice positively charged ion is preferably a Zn ion, a Mg ion, a Cu ion, or an Fe ion, more preferably a Zn ion, wherein more preferably, the Lewis acid comprises, preferably is, one or more of $ZnBr_2$, $ZnCl_2$, and $ZnI_2$, more preferably $ZnBr_2$, and wherein the base is preferably an organic base, more preferably an organic nitrogenous base, wherein more preferably, the base comprises one or more of an amine, an amidine, and a heteroaromatic compound comprising a basic ring-nitrogen atom, more preferably one or more of ethyldiisopropylamine, triethylamine, diethylamine, 1,8-diazabicycloundec-7-ene, pyridine, quinoline, isoquinoline, acridine, pyrazine, imidazole, benzimidazole, and pyrazole, wherein more preferably, the base comprises, preferably is, triethylamine. Consequently, the present invention also relates to the use of this mixture for preparing a compound of formula (IV) or for preparing a compound of formula (III) or for preparing a compound of formula (II) or for preparing a compound of formula (I).

Further, the present invention is illustrated by the following embodiments and combinations of embodiments as given by the respective dependencies and references.

1. A process for preparing a compound of formula (I)

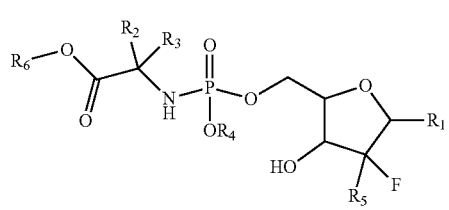

(I)

or a salt thereof, the process comprising
(i) providing a compound of formula (III)

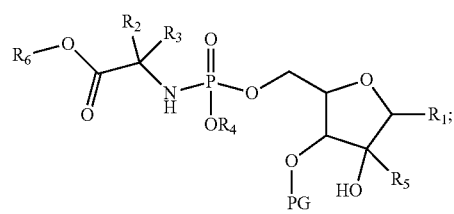

(III)

(ii) reacting the compound of formula (III) with a fluorinating agent, obtaining a compound of formula (II)

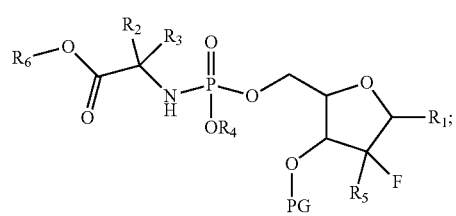

(II)

(iii) optionally isolating the compound of formula (II) from the reaction mixture obtained in (ii);

(iv) deprotecting the compound of formula (II) obtaining the compound of formula (I);
(v) preferably purifying the compound of formula (I).

2. The process of embodiment 1, wherein
$R_1$ is an optionally derivatized purinyl residue, including an adenine residue and a guanine residue, or an optionally derivatized pyrimidinyl residue, including a cytosine residue, a thymine residue and an uracil residue, linked to the furanose ring according to formula (III) through a carbon or nitrogen atom of said residue;
$R_2$ and $R_3$ are independently H or $C_1$-$C_6$ alkyl optionally substituted with at least one of OH, $C_1$-$C_6$ alkoxy, aryl, heteroaryl, $C_1$-$C_6$ alkyl, $C_3$-$C_6$ cycloalkyl, F, Cl, Br, I, $NO_2$, C(O)OH, CHO, C(O)($C_1$-$C_6$ alkyl), C(O)(aryl), C(O)O($C_1$-$C_6$ alkyl), C(O)$ONH_2$, C(O)ONH($C_1$-$C_6$ alkyl) and CN;
$R_4$ is phenyl, naphthyl, quinolinyl, isoquinolinyl, quinazolinyl or quinoxalinyl, each optionally substituted with at least one of $C_1$-$C_6$ alkyl, $C_1$-$C_6$ alkoxy, $C_3$-$C_6$ cycloalkyl, aryl, halogen, C(O)OH, CHO, C(O)($C_1$-$C_6$ alkyl), C(O)(aryl), C(O)O($C_1$-$C_6$ alkyl), C(O)$ONH_2$, C(O)ONH($C_1$-$C_6$ alkyl) and CN;
$R_5$ is H, $NH_2$, $NHR_{51}$, $NR_{51}R_{52}$, C(O)$NH_2$, C(O)$NHR_{51}$, C(O)$NR_{51}R_{52}$, $C_1$-$C_6$ alkyl optionally substituted with $C_1$-$C_6$ alkyl, or $C_3$-$C_{10}$ cycloalkyl optionally substituted with $C_1$-$C_6$ alkyl, wherein $R_{51}$ and $R_{52}$ are independently $C_1$-$C_6$ alkyl;
$R_6$ is $C_1$-$C_6$ alkyl or $C_3$-$C_{10}$ cycloalkyl optionally substituted with at least one of $C_1$-$C_6$ alkyl and aryl;
PG is an inert electron withdrawing hydroxyl protecting group.

3. The process of embodiment 1 or 2, wherein according to (i), providing the compound of formula (III) comprises
(i.1) providing a compound of formula (IV)

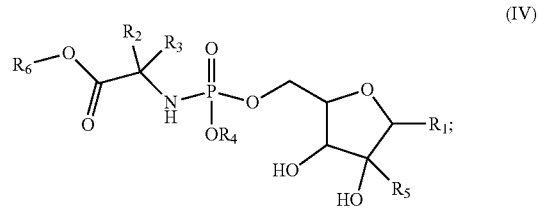

(IV)

(i.2) reacting the compound of formula (IV) with a hydroxyl protecting agent Y-PG, obtaining the compound of formula (III);
(i.3) optionally purifying the compound of formula (III).

4. The process of embodiment 1 or 2, wherein the compound of formula (III), provided according to (i), is obtainable or obtained by a process comprising
(i.1) providing a compound of formula (IV)

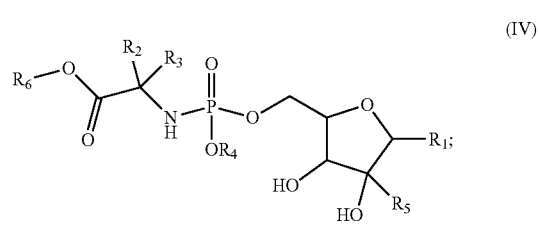

(IV)

(i.2) reacting the compound of formula (IV) with a hydroxyl protecting agent Y-PG, obtaining the compound of formula (III);
(i.3) optionally purifying the compound of formula (III).
5. A process for preparing a compound of formula (III), said process comprising
(i.1) providing a compound of formula (IV)

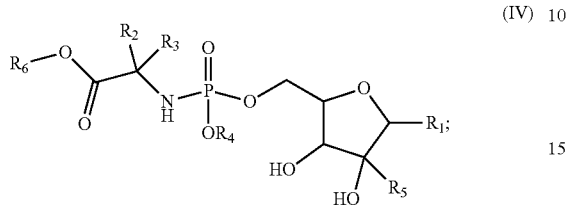

(i.2) reacting the compound of formula (IV) with a hydroxyl protecting agent Y-PG, obtaining the compound of formula (III);
(i.3) optionally purifying the compound of formula (III);
wherein the residues $R_1$, $R_2$, $R_3$, $R_4$, $R_5$ and $R_6$ are as defined in embodiment 2.
6. The process of any one of embodiments 3 to 5, wherein according to (i.1), providing the compound of formula (IV) comprises
(i.1.1) reacting a compound of formula (V)

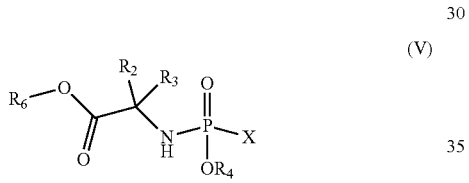

wherein the residue X of the compound of formula (V) according to (i.1.1) is preferably a leaving group which is suitable for a nucleophilic substitution reaction, with a compound of formula (VI)

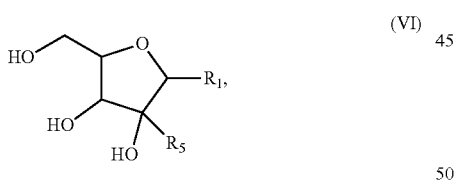

obtaining the compound of formula (IV);
(i.1.2) preferably purifying the compound of formula (IV);
7. The process of any one of embodiments 3 to 5, wherein the compound of formula (IV), provided according to (i.1), is obtainable or obtained by a process comprising
(i.1.1) reacting a compound of formula (V)

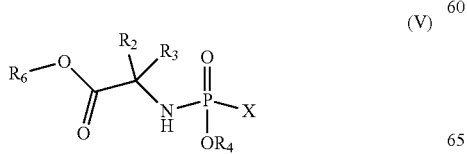

wherein the residue X of the compound of formula (V) according to (i.1.1) is preferably a leaving group which is suitable for a nucleophilic substitution reaction, with a compound of formula (VI)

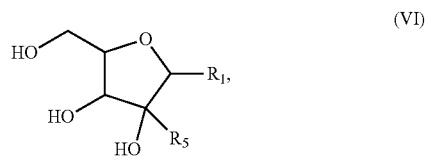

obtaining the compound of formula (IV);
(i.1.2) preferably purifying the compound of formula (IV).
8. A process for preparing a compound of formula (IV), said process comprising
(i.1.1) reacting a compound of formula (V)

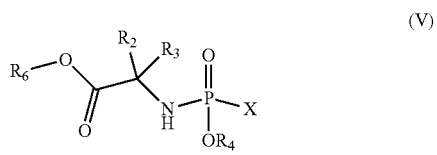

wherein the residue X of the compound of formula (V) according to (i.1.1) is preferably a leaving group which is suitable for a nucleophilic substitution reaction, with a compound of formula (VI)

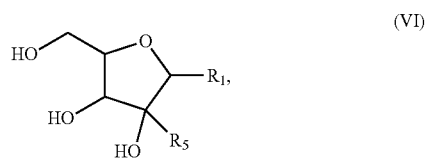

obtaining the compound of formula (IV);
(i.1.2) preferably purifying the compound of formula (IV);
wherein the residues $R_1$, $R_2$, $R_3$, $R_4$, $R_5$ and $R_6$ are as defined in embodiment 2;
9. The process of any one of embodiments 1 to 8, wherein the compound of formula (I) is

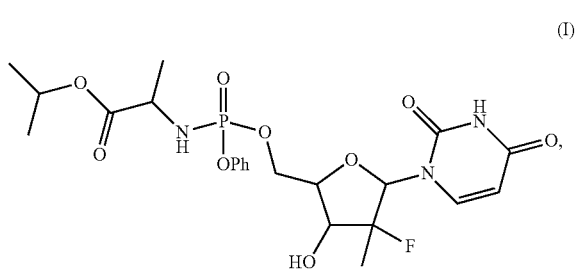 [SMILES: CC(C)OC(=O)C(C)NP(=O)(OCC1OC(n2ccc(=O)[nH]c2=O)C(C)(F)C1O)Oc1ccccc1]

the compound of formula (II) is

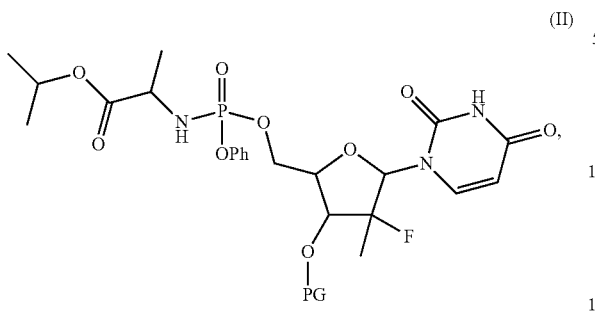

the compound of formula (III) is

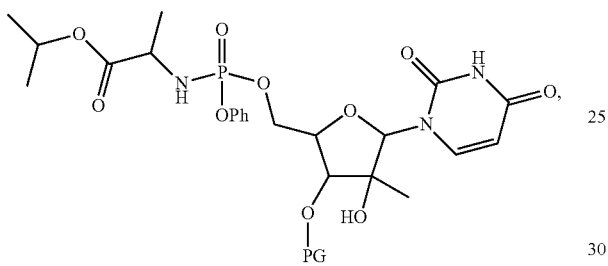

the compound of formula (IV) is

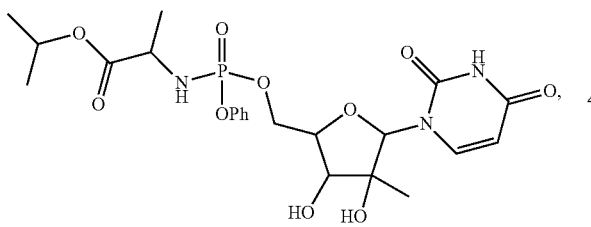

the compound of formula (V) is

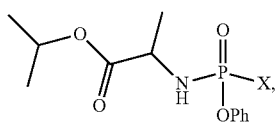

and the compound of formula (VI) is

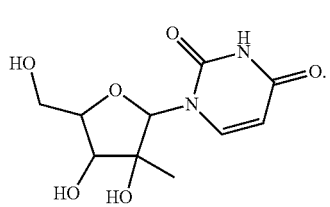

10. A process for preparing a compound of formula (I)

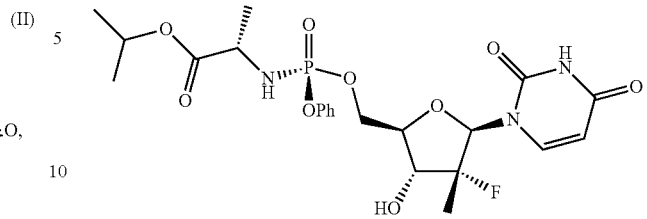

or a salt thereof, the process comprising
(i) providing a compound of formula (III)

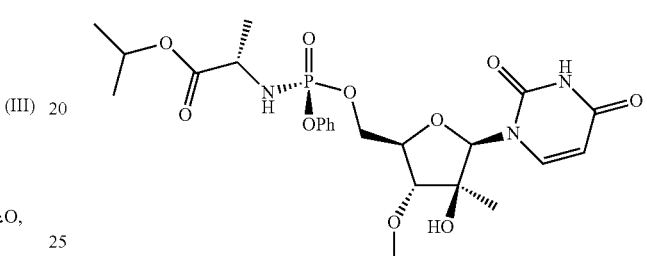

wherein PG is an inert electron withdrawing hydroxyl protecting group;
(ii) reacting the compound of formula (III) with a fluorinating agent, obtaining a compound of formula (II)

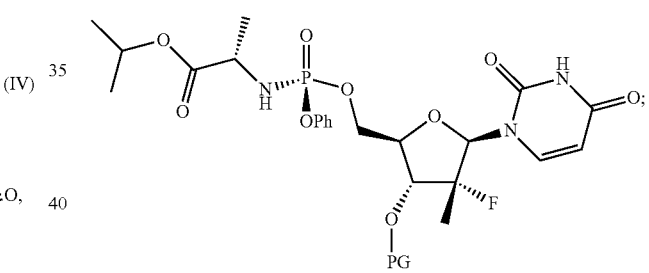

(iii) optionally isolating the compound of formula (II) from the reaction mixture obtained in (ii);
(iv) deprotecting the compound of formula (II) obtaining the compound of formula (I).

11. The process of any one of embodiments 1 to 10, preferably 10, wherein the inert electron withdrawing hydroxyl protecting group PG is
either $C(O)CH_nX_{3-n}$ with X being halogen, preferably F, Cl, Br, I, and n being 0, 1, or 2;
or $SO_2Z$ with Z being Me (methyl), Ph (phenyl), p-Me-Ph (tosyl), p-$NO_2$-Ph (para-nosyl), o-$NO_2$-Ph (ortho-nosyl), o-$CF_3$-Ph (ortho-trifluoromethylphenyl) or $CF_3$ (triflyl); or a residue of formula (E)

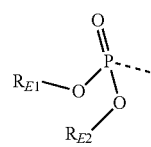

wherein the dotted line indicates the bond via which the residue is linked to the oxygen atom, wherein $R_{E1}$ and R$_{E2}$ are independently from each other alkyl or aryl, or together are a (CH$_2$)$_q$ group forming a ring together with the oxygen atoms to which R$_{E1}$ and R$_{E2}$ are bound and the P atom to which said oxygen atoms are bound, where q is 2, 3, 4, 5, 6, or 7, preferably 2, 3, or 4; or CH=CH$_2$—CO$_2$R$_x$ or C(O)—CH$_2$—CO$_2$R$_x$ where R$_x$ is alkyl, or aryl, or cycloalkyl.

12. The process of embodiment 11, wherein R$_{E1}$ is C$_1$-C$_6$ alkyl, preferably C$_1$-C$_4$ alkyl, more preferably C$_1$-C$_2$ alkyl, or aryl, preferably phenyl or naphthyl, and wherein R$_{E2}$ is C$_1$-C$_6$ alkyl, preferably C$_1$-C$_4$ alkyl, more preferably C$_1$-C$_2$ alkyl, or C$_3$-C$_6$ cycloalkyl, preferably C$_5$-C$_6$ cycloalkyl, or aryl, preferably phenyl or naphthyl; or wherein R$_x$ is C$_1$-C$_6$ alkyl, preferably C$_1$-C$_4$ alkyl, more preferably C$_1$-C$_2$ alkyl, or C$_3$-C$_6$ cycloalkyl, preferably C$_5$-C$_6$ cycloalkyl, or aryl, preferably phenyl or naphthyl.

13. The process of any one of embodiments 1 to 11, preferably 10 or 11, wherein the inert electron withdrawing hydroxyl protecting group PG is C(O)CH$_n$F$_{3-n}$ with n being 0, 1, or 2.

14. The process of embodiment 13, wherein the inert electron withdrawing hydroxyl protecting group PG is C(O)CF$_3$ and wherein the compound of formula (III) is preferably

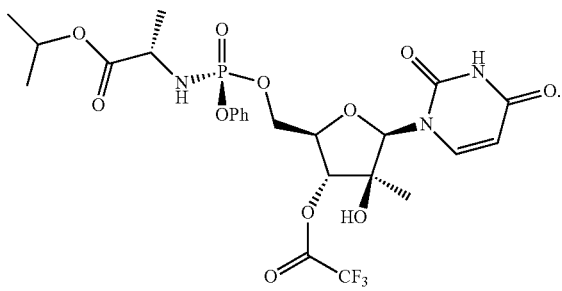

(III)

15. The process of any one of embodiments 1 to 14, preferably 10 to 14, wherein the fluorinating agent according to (ii) comprises one or more of (diethylamino)difluorosulfonium tetrafluoroborate and difluoro(morpholino)sulfonium tetrafluoroborate.

16. The process of any one of embodiments 1 to 15, preferably 10 to 15, wherein the fluorinating agent according to (ii) comprises, preferably is, (diethylamino)difluorosulfonium tetrafluoroborate.

17. The process of any one of embodiments 1 to 16, preferably 10 to 16, wherein the inert electron withdrawing hydroxyl protecting group PG is C(O)CF$_3$ and the fluorinating agent according to (ii) is (diethylamino)difluorosulfonium tetrafluoroborate.

18. The process of any one of embodiments 1 to 17, preferably 10 to 17, wherein prior to the reacting according to (ii), the molar ratio of the fluorinating agent relative to the compound of formula (III) is in the range of from 0.1:1 to 3:1, preferably in the range of from 1.25:1 to 2:1, more preferably in the range of from 1.45:1 to 1.65:1.

19. The process of any one of embodiments 1 to 18, preferably 10 to 18, wherein according to (ii), the compound of formula (III) is reacted with the fluorinating agent in the presence of a fluorination promotor.

20. The process of embodiment 19, wherein the fluorination promotor comprises, preferably is, one or more of triethylamine trihydrofluoride (TEA 3HF), triethylamine dihydrofluoride (TEA 2HF), and diazabicycloundec-7-ene (DBU), preferably one or more of triethylamine trihydrofluoride and triethylamine dihydrofluoride.

21. The process of embodiment 19 or 20, wherein prior to the reacting according to (ii), the molar ratio of the fluorination promotor relative to the compound of formula (III) is in the range of from 0.1:1 to 3:1, preferably in the range of from 1.75:1 to 2.5:1, more preferably in the range of from 1.95:1 to 2.05:1.

22. The process of any one of embodiments 1 to 21, preferably 10 to 21, wherein according to (ii), the compound of formula (III) is reacted with the fluorinating agent in a solvent.

23. The process of embodiment 22, wherein the solvent comprises, preferably is, an organic solvent, preferably an aprotic organic solvent.

24. The process of embodiment 22 or 23, wherein the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran.

25. The process of any one of embodiments 22 to 24, wherein the solvent comprises, preferably is, dichloromethane, preferably anhydrous dichloromethane.

26. The process of any one of embodiments 1 to 25, preferably 10 to 25, wherein according to (ii), the reacting is carried out at a temperature in the range of from 0 to 40° C., preferably in the range of from 10 to 30° C., more preferably in the range of from 20 to 25° C.

27. The process of any one of embodiments 1 to 26, preferably 10 to 26, wherein according to (ii), the reacting is carried out for a period of time in the range of from 0.1 to 24 h, preferably in the range of from 0.2 to 6 h, more preferably in the range of from 0.5 to 2 h.

28. The process of any one of embodiments 1 to 27, preferably 10 to 27, comprising
(iii) isolating the compound of formula (II) from the reaction mixture obtained in (ii).

29. The process of embodiment 28, wherein the isolating according to (iii) comprises
(iii.1) extracting the compound of formula (II) from the mixture obtained in (ii);
(iii.2) separating the compound of formula (II) from the mixture obtained in (iii.1).

30. The process of embodiment 29, wherein the isolating according to (iii) or the separating according to (iii.2) comprises filtration, centrifugation, drying, or a combination of two or more thereof 31. The process of any one of embodiments 1 to 27, preferably 10 to 27, wherein after (ii) and before (iv), the compound of formula (II) is not isolated from the reaction mixture obtained in (ii).

32. The process of embodiment 31, wherein the mixture obtained in (ii) is used as starting mixture for the deprotecting according to (iv).

33. The process of any one of embodiments 1 to 32, preferably 10 to 32, more preferably 31 or 32, wherein the deprotecting according to (iv) comprises
(iv.1) reacting the compound of formula (II) with an aqueous system, obtaining the compound of formula (I).

34. The process of embodiment 33, wherein the aqueous system comprises water and an acid, preferably an inorganic acid.

35. The process of embodiment 34, wherein the acid is one or more of HCl, H$_2$SO$_4$, HNO$_3$, NH$_4$Cl, HCOOH, HOAc, or a buffer system having a pH in the range of from 4 to 7, the inorganic acid preferably comprising, more preferably being, HCl.

36. The process of embodiment 34 or 35, wherein the aqueous system has a pH in the range of from 0 to 6, preferably of from 1 to 6, more preferably of from 1 to 2, as determined using a pH sensitive glass electrode.

37. The process of any one of embodiments 34 to 36, wherein at least 99 weight-%, preferably at least 99.5 weight-%, more preferably at least 99.9 weight-% of the aqueous system consist of water and the acid.

38. The process of any one of embodiments 33 to 37, wherein the reacting according to (iv.1) is carried out at a temperature in the range of from 0 to 40° C., preferably in the range of from 10 to 35° C., more preferably in the range of from 20 to 30° C.

39. The process of any one of embodiments 33 to 38, wherein according to (iv.1), the compound of formula (I) is obtained comprised in the solvent as defined in any one of embodiments 22 to 25, preferably 23 to 25, more preferably 24 or 25, more preferably 25.

40. The process of any one of embodiments 33 to 39, preferably 39, comprising
(iv.2) working up the reaction mixture obtained in (iv.1), obtaining the compound of formula (I).

41. The process of embodiment 40, wherein the working up according to (iv.2) comprises
(iv.2.1) separating the organic phase from the aqueous phase;
(iv.2.2) optionally washing the aqueous phase with an organic solvent, preferably a solvent as defined in any one of embodiments 23 to 25, preferably 24 or 25, more preferably 25.
(iv.2.3) optionally drying the organic phase obtained in (iv.2.1), and optionally the organic phase obtained in (iv.2.2), obtaining the compound of formula (I).

42. The process of any one of embodiments 1 to 41, preferably 10 to 41, more preferably 33 to 41, more preferably 41, comprising
(v) purifying the compound of formula (I).

43. The process of embodiment 42, wherein the purifying according to (v) comprises
(v.1) crystallizing the compound of formula (I), obtaining the compound of formula (I) in its mother liquor, preferably from a solvent comprising one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably dichloromethane;
(v.2) preferably separating the crystallized compound of formula (I) from its mother liquor, obtaining the compound of formula (I) in crystalline form, said separating preferably comprising
(v.2.1) subjecting the mother liquor comprising the crystallized compound of formula (I) to filtration, obtaining a filter cake comprising the compound of formula (I);
(v.2.2) optionally washing the filter cake comprising the compound of formula (I), preferably using a washing agent comprising one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably dichloromethane;
(v.2.3) drying the optionally washed filter cake, obtaining the compound of formula (I).

44. The process of any one of embodiments 1 to 43, preferably 10 to 43, wherein according to (i), providing the compound of formula (III) comprises
(i.1) providing a compound of formula (IV)

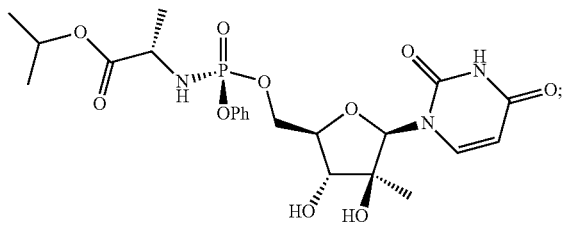

(IV)

(i.2) reacting the compound of formula (IV) with a hydroxyl protecting agent Y-PG, obtaining the compound of formula (III);
(i.3) optionally purifying the compound of formula (III).

45. The process of any one of embodiments 1 to 43, preferably 10 to 43, wherein the compound of formula (III), provided according to (i), is obtainable or obtained by a process comprising
(i.1) providing a compound of formula (IV)

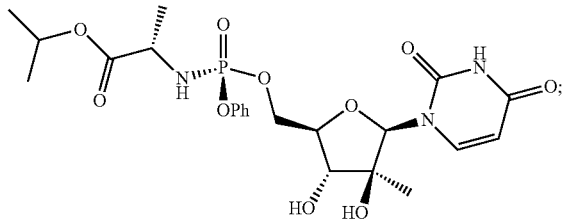

(IV)

(i.2) reacting the compound of formula (IV) with a hydroxyl protecting agent Y-PG, obtaining the compound of formula (III);
(i.3) optionally purifying the compound of formula (III).

46. A process for preparing a compound of formula (III), said process comprising
(i.1) providing a compound of formula (IV)

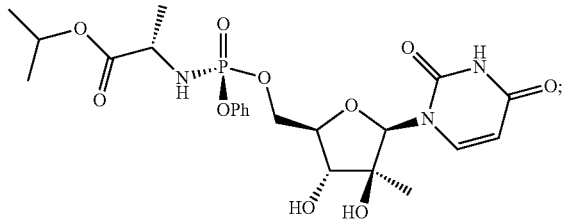

(IV)

(i.2) reacting the compound of formula (IV) with a hydroxyl protecting agent Y-PG, obtaining the compound of formula (III);
(i.3) optionally purifying the compound of formula (III).

47. The process of any one of embodiments 44 to 46, wherein in the hydroxyl protecting agent Y-PG, the group PG is as defined in any one of embodiments 11 to 13, preferably 12 or 13, more preferably 13.
48. The process of embodiment 47, wherein in the hydroxyl protecting agent Y-PG, Y is a halide, preferably Cl.
49. The process of embodiment 47, wherein the hydroxyl protecting agent Y-PG is trifluoroacetic anhydride.
50. The process of any one of embodiments 44 to 49, wherein prior to the reacting according to (i.2), the molar ratio of the hydroxyl protecting agent Y-PG relative to the compound of formula (IV) is in the range of from 1:1 to 3:1, preferably in the range of from 1.01:1 to 2:1, more preferably in the range of from 1.02:1 to 1.5:1.
51. The process of any one of embodiments 44 to 50, wherein according to (i.2), the reacting is carried out at a temperature in the range of from 0 to 40° C., preferably in the range of from 10 to 30° C., more preferably in the range of from 20 to 25° C.
52. The process of any one of embodiments 44 to 51, wherein according to (i.2), the reacting is carried out for a period of time in the range of from 0.1 to 24 h, preferably in the range of from 0.2 to 6 h, more preferably in the range of from 0.5 to 3 h.
53. The process of any one of embodiments 44 to 52, wherein according to (i.2), the compound of formula (IV) is reacted with the hydroxyl protecting agent Y-PG in a solvent.
54. The process of embodiment 53, wherein the solvent comprises, preferably is, an organic solvent, preferably an aprotic organic solvent.
55. The process of embodiment 53 or 54, wherein the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran.
56. The process of any one of embodiments 53 to 55, wherein the solvent comprises, preferably is, dichloromethane, preferably anhydrous dichloromethane.
57. The process of any one of embodiments 53 to 56, wherein the solvent according to (i.2) is the solvent of (ii) as defined in any one of embodiments 23 to 25.
58. The process of any one of embodiments 44 to 57, preferably 51 to 57, comprising
(i.3) purifying the compound of formula (III).
59. The process of embodiment 58, wherein the purifying according to (i.3) comprises crystallization of the compound of formula (III).
60. The process of any one of embodiments 44 to 57, preferably 51 to 57, wherein after (i.2), the compound of formula (III) is not purified.
61. The process of embodiment 60, preferably insofar as embodiment 60 is dependent on any one of embodiments 51 to 57, wherein after (i.2) and before (ii), the solvent is at least partially, preferably essentially completely separated from the compound of formula (III), preferably by evaporation.
62. The process of embodiment 60, preferably insofar as embodiment 60 is dependent on any one of embodiments 51 to 57, wherein after (i.2) and before (ii), the solvent is not separated from the compound of formula (III).

63. The process of embodiment 62, wherein the reaction mixture obtained from (i.2) is directly employed in (ii).
64. The process of any one of embodiments 44 to 63, wherein according to (i.1), providing the compound of formula (IV) comprises
(i.1.1) reacting a compound of formula (V)

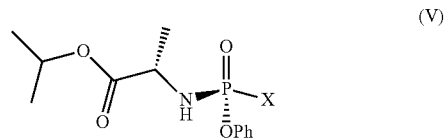

with a compound of formula (VI)

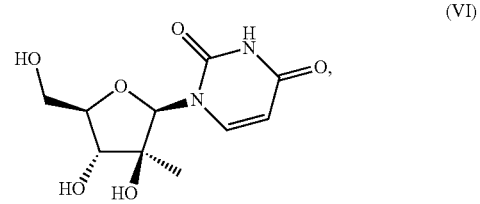 [SMILES: C[C@]1(O)[C@H](O)[C@@H](CO)O[C@H]1n1ccc(=O)[nH]c1=O]

obtaining the compound of formula (IV);
(i.1.2) preferably purifying the compound of formula (IV).
65. The process of any one of embodiments 44 to 63, wherein the compound of formula (IV), provided according to (i.1), is obtainable or obtained by a process comprising
(i.1.1) reacting a compound of formula (V)

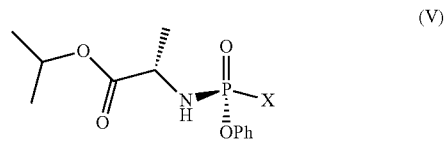

with a compound of formula (VI)

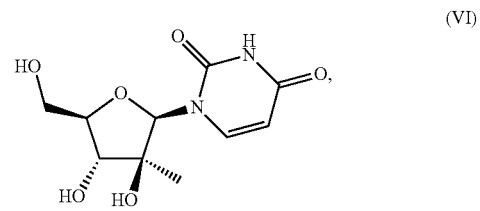 [SMILES: C[C@]1(O)[C@H](O)[C@@H](CO)O[C@H]1n1ccc(=O)[nH]c1=O]

obtaining the compound of formula (IV);
(i.1.2) preferably purifying the compound of formula (IV).
66. A process for preparing a compound of formula (IV), said process comprising
(i.1.1) reacting a compound of formula (V)

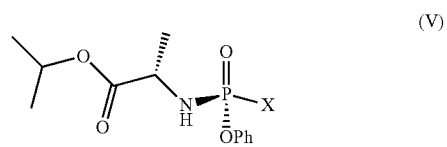

with a compound of formula (VI)

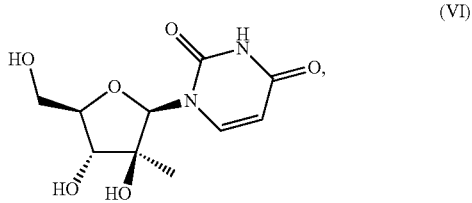 [SMILES: C[C@]1(O)[C@H](O)[C@@H](CO)O[C@H]1n1ccc(=O)[nH]c1=O]
(VI)

obtaining the compound of formula (IV);
(i.1.2) preferably purifying the compound of formula (IV).

67. The process of any one of embodiments 64 to 66, wherein the residue X of the compound of formula (V) according to (i.1.1) is a leaving group which is suitable for a nucleophilic substitution reaction.

68. The process of embodiment 67, wherein —X is —(Z—)$_n$ R$_Y$ where n is 0 or 1 and Z is O, N or S.

69. The process of embodiment 68, wherein n is 1; and R$_Y$ is alkyl; or R$_Y$ is aryl; or R$_Y$ is heteroaryl, each alkyl or aryl or heteroaryl optionally substituted with one or more electron withdrawing groups; preferably aryl optionally substituted with one or more electron withdrawing groups; more preferably phenyl optionally substituted with one or more electron withdrawing groups, wherein the one or more electron withdrawing groups are preferably F, Cl, Br, I, or NO$_2$; or R$_Y$ is a residue of formula (A)

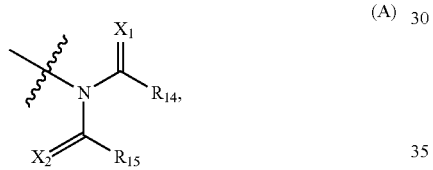
(A)

a residue of formula (B)

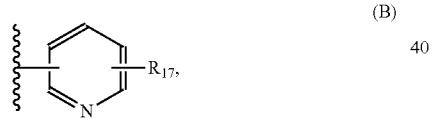
(B)

a residue of formula (C)

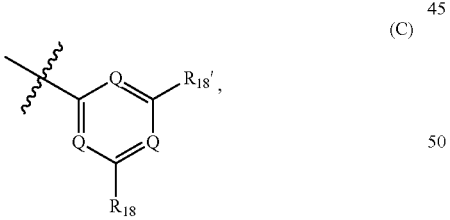
(C)

or a residue of formula (D)

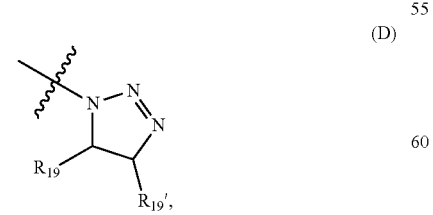
(D)

wherein at each occurrence
X$_1$ and X$_2$ are independently O or S;
R$_{14}$ and R$_{15}$ are independently H, OH, NH$_2$, C$_1$-C$_6$ alkyl or C$_1$-C$_6$ alkoxy, or R$_{14}$ and R$_{15}$, together with the structure —C—N—C— according to formula (A), form an optionally substituted, 5-, 6-, or 7-membered saturated or partially unsaturated ring, wherein said ring is optionally fused to a 5- or 6-membered, optionally substituted ring which is a C$_5$-C$_6$ cycloalkyl, an aryl or a heterocycle comprising one or more heteroatoms independently being N, O or S;

R$_{17}$ is an electron-withdrawing group, preferably F, Cl, Br, I, NO$_2$, CHO, C(O)OH, C(O)—(C$_1$-C$_6$)alkyl, CN, or C(O)Cl;

R$_{18}$ and R$_{18'}$ are independently F, Cl, Br, I, or C$_1$-C$_6$ alkoxy;

each Q is independently C or N, wherein at least one Q is N;

R$_{19}$ and R$_{19'}$ are independently H, OH, NH$_2$, C$_1$-C$_6$ alkyl optionally substituted with at least one of OH and NH$_2$, or C$_1$-C$_6$ alkoxy optionally substituted with at least one of OH and NH$_2$; or R$_{19}$ and R$_{19'}$ taken together form an optionally substituted 5-, 6-, or 7-membered saturated or partially unsaturated or aromatic ring, wherein the ring is optionally fused to a 5- or 6-membered, optionally substituted ring which is a C$_5$-C$_6$ cycloalkyl, an aryl, preferably benzo, or a heterocycle comprising one or more heteroatoms independently being N, O or S, the 5- or 6-membered optionally substituted ring preferably being heteroaryl;

R$_{20}$, R$_{21}$, R$_{22}$ and R$_{23}$ are each independently H, aryl, or C$_1$-C$_6$ alkyl optionally substituted with at least one of C$_1$-C$_6$ alkoxy optionally substituted with at least one of OH and NH$_2$, or R$_{20}$ and R$_{22}$, or R$_{20}$ and R$_{23}$, or R$_{21}$ and R$_{22}$, or R$_{21}$ and R$_{23}$ when taken together form an optionally substituted 5-, 6-, or 7-membered saturated or partially unsaturated or aromatic ring which is an aryl, preferably benzo, or a heterocycle comprising one or more heteroatoms independently being N, O or S, the 5-, 6-, or 7-membered saturated or partially unsaturated or aromatic ring preferably being heteroaryl.

70. The process of embodiment 68, wherein n is 1 and R$_Y$ is alkyl, aryl, or heteroaryl, each optionally substituted with one or more electron-withdrawing groups, preferably aryl optionally substituted with one or more electron-withdrawing groups, more preferably phenyl optionally substituted with one or more electron-withdrawing groups, wherein the one or more electron-withdrawing groups are preferably F, Cl, Br, I, or NO$_2$.

71. The process of embodiment 68, wherein n is 1 and R$_Y$ is a residue of formula (A)

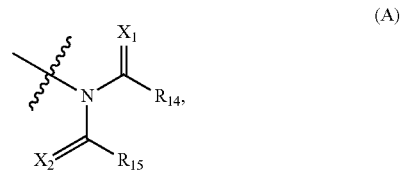
(A)

a residue of formula (B)

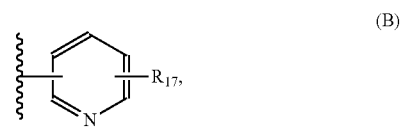
(B)

a residue of formula (C)

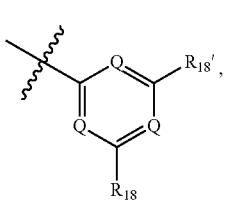

or a residue of formula (D)

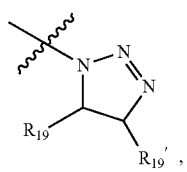

wherein at each occurrence $X_1$ and $X_2$ are independently O or S;

$R_{14}$ and $R_{15}$ are independently H, OH, $NH_2$, $C_1$-$C_6$ alkyl or $C_1$-$C_6$ alkoxy, or $R_{14}$ and $R_{15}$, together with the structure —C—N—C— according to formula (A), form an optionally substituted, 5-, 6-, or 7-membered saturated or partially unsaturated ring, wherein said ring is optionally fused to a 5- or 6-membered, optionally substituted ring which is a $C_5$-$C_6$ cycloalkyl, an aryl or a heterocycle comprising one or more heteroatoms independently being N, O or S;

$R_{17}$ is an electron-withdrawing group, preferably F, Cl, Br, I, $NO_2$, CHO, C(O)OH, C(O)—($C_1$-$C_6$)alkyl, CN, or C(O)Cl;

$R_{18}$ and $R_{18'}$ are independently F, Cl, Br, I, or $C_1$-$C_6$ alkoxy;

each Q is independently C or N, wherein at least one Q is N;

$R_{19}$ and $R_{19'}$ are independently H, OH, $NH_2$, $C_1$-$C_6$ alkyl optionally substituted with at least one of OH and $NH_2$, or $C_1$-$C_6$ alkoxy optionally substituted with at least one of OH and $NH_2$; or $R_{19}$ and $R_{19'}$, taken together form an optionally substituted 5-, 6-, or 7-membered saturated or partially unsaturated or aromatic ring, wherein the ring is optionally fused to a 5- or 6-membered, optionally substituted ring which is a $C_5$-$C_6$ cycloalkyl, an aryl, preferably benzo, or a heterocycle comprising one or more heteroatoms independently being N, O or S, the 5- or 6-membered optionally substituted ring preferably being heteroaryl;

$R_{20}$, $R_{21}$, $R_{22}$ and $R_{23}$ are each independently H, aryl, or $C_1$-$C_6$ alkyl optionally substituted with at least one of $C_1$-$C_6$ alkoxy optionally substituted with at least one of OH and $NH_2$, or $R_{20}$ and $R_{22}$, or $R_{20}$ and $R_{23}$, or $R_{21}$ and $R_{22}$, or $R_{21}$ and $R_{23}$ when taken together form an optionally substituted 5-, 6-, or 7-membered saturated or partially unsaturated or aromatic ring which is an aryl, preferably benzo, or a heterocycle comprising one or more heteroatoms independently being N, O or S, the 5-, 6-, or 7-membered saturated or partially unsaturated or aromatic ring preferably being heteroaryl.

72. The process of embodiment 71, wherein n is 1 and $R_Y$ is a residue of formula (A)

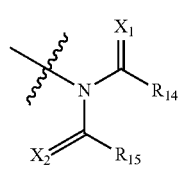

wherein $X_1$ and $X_2$ are independently O or S;

$R_{14}$ and $R_{15}$ are independently H, OH, $NH_2$, $C_1$-$C_6$ alkyl or $C_1$-$C_6$ alkoxy, or $R_{14}$ and $R_{15}$, together with the structure —C—N—C— according to formula (A), form an optionally substituted, 5-, 6-, or 7-membered saturated or partially unsaturated ring, wherein said ring is optionally fused to a 5- or 6-membered, optionally substituted ring which is a $C_5$-$C_6$ cycloalkyl, an aryl or a heterocycle comprising one or more heteroatoms independently being N, O or S, wherein $R_Y$ is preferably a residue of formula (Ab)

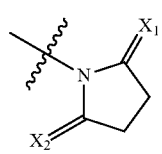

or a residue of formula (Ac)

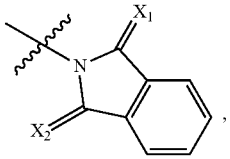

wherein $X_1$ is preferably O and $X_2$ is preferably O.

73. The process of embodiment 68, wherein n is 0 and $R_Y$ is a residue of formula (A1)

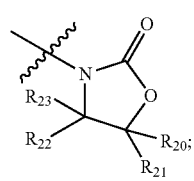

wherein at each occurrence $R_{20}$, $R_{21}$, $R_{22}$ and $R_{23}$ are each independently H, aryl, or $C_1$-$C_6$ alkyl optionally substituted with at least one of $C_1$-$C_6$ alkoxy optionally substituted with at least one of OH and $NH_2$; or $R_{20}$ and $R_{22}$, or $R_{20}$ and $R_{23}$, or $R_{21}$ and $R_{22}$, or $R_{21}$ and $R_{23}$ when taken together form an optionally substituted 5-, 6-, or 7-membered saturated or partially unsaturated or aromatic ring which is an aryl, preferably benzo, or a heterocycle comprising one or more heteroatoms independently being N, O or S, the 5-, 6-, or 7-membered saturated or partially unsaturated or aromatic ring preferably being heteroaryl.

74. The process of any one of embodiments 64 to 67, wherein —X is —Cl.

75. The process of any one of embodiments 64 to 74, wherein according to (i.1.1), the compound of formula (V) is reacted with the compound of formula (VI) in the presence of a Lewis acid, wherein the Lewis acid preferably comprises a twice positively charged ion or a three times positively charged ion, more preferably a twice positively charged metal ion or a three times positively charged metal ion.

76. The process of embodiment 75, wherein the twice positively charged ion is a Zn ion, a Mg ion, a Cu ion, or an Fe ion, preferably a Zn ion, wherein more preferably, the Lewis acid comprises, preferably is, one or more of $ZnBr_2$, $ZnCl_2$, and $ZnI_2$, more preferably $ZnBr_2$.

77. The process of embodiment 75, wherein the one or more Lewis acid is one or more of $ZnBr_2$, $ZnCl_2$, $ZnI_2$, $MgBr_2$, $MgBr_2$—$OEt_2$, $CuCl_2$, $Cu(acetylacetonate)_2$, and $Fe(II)$ fumarate.

78. The process of embodiment 75, wherein the three times positively charged ion is a Mn ion, wherein more preferably, the Lewis acid comprises, preferably is, $Mn(acetylacetonate)_3$.

79. The process of any one of embodiments 74 to 78, wherein prior to the reaction according to (i.1.1), the molar ratio of the Lewis acid relative to the compound of formula (VI) is in the range of from 0.1:1 to 5:1, preferably in the range of from 0.2:1 to 5:1, more preferably in the range of from 0.5:1 to 3:1, more preferably in the range of from 0.75:1 to 1.5:1.

80. The process of any one of embodiments 64 to 79, wherein according to (i.1.1), the compound of formula (V) is reacted with the compound of formula (VI) in the presence of a base, preferably an organic base, more preferably an organic nitrogenous base.

81. The process of embodiment 80, wherein the organic base comprises one or more of an amine, an amidine, and a heteroaromatic compound comprising a basic ring-nitrogen atom, preferably one or more of ethyldiisopropylamine, triethylamine, diethylamine, 1,8-diazabicycloundec-7-ene, pyridine, quinoline, isoquinoline, acridine, pyrazine, imidazole, benzimidazole, and pyrazole.

82. The process of embodiment 80 or 81, wherein the organic base comprises, preferably is, triethylamine.

83. The process of any one of embodiments 80 to 82, wherein prior to the reacting according to (i.1.1), the molar ratio of the base relative to the compound of formula (VI) is in the range of from 0.1:1 to 5:1, preferably in the range of from 1:1 to 5:1, more preferably in the range of from 2:1 to 5:1, more preferably in the range of from 2.5:1 to 4:1, more preferably in the range of from 2.5:1 to 3.5:1.

84. The process of any one of embodiments 64 to 83, wherein prior to the reacting according to (i.1.1), the molar ratio of the compound of formula (V) relative to the compound of formula (VI) is in the range of from 0.5:1 to 5:1, preferably in the range of from 0.8:1 to 2:1, more preferably in the range of from 0.9:1 to 1.2:1.

85. The process of any one of embodiments 64 to 84, wherein the reacting according to (i.1.1) is carried out at a temperature in the range of from 0 to 80° C., preferably in the range of from 0 to 25° C., more preferably in the range of from 0 to 5° C.

86. The process of any one of embodiments 64 to 85, wherein the reacting according to (i.1.1) is carried out for a period of time in the range of from 0.5 to 48 h, preferably in the range of from 1 to 36 h, more preferably in the range of from 2 to 24 h.

87. The process of any one of embodiments 64 to 86, wherein according to (i.1.1), the compound of formula (V) is reacted with the compound of formula (VI) in the presence of a solvent, preferably an organic solvent, more preferably an aprotic organic solvent.

88. The process of embodiment 87, wherein the solvent comprises one or more of methylene chloride, methyl tert-butyl ether, tetrahydrofuran, dimethylsulphoxide, and dimethylformamide, wherein more preferably, the solvent comprises, preferably is, tetrahydrofuran.

89. The process of any one of embodiments 64 to 88, preferably 87 or 88, comprising (i.1.2) purifying the compound of formula (IV) comprising working up the reaction mixture obtained in (i.1.1), obtaining the purified compound of formula (IV).

90. The process of embodiment 89, wherein the working up according to (i.1.2) comprises (i.1.2.1) subjecting the reaction mixture obtained from (i.1.1) to solid-liquid separation, preferably by filtration, preferably followed by washing with a washing agent, wherein the washing agent is preferably a solvent as defined in embodiment 85 or 86, preferably 86;

(i.1.2.2) drying the preferably washed solid, obtaining a purified compound of formula (IV).

91. The process of embodiment 90, comprising (i.1.2.3) dissolving the solid obtained from (i.1.2.2) in a solvent, preferably comprising one or more of dichloromethane, dichloroethane, chloroform, toluene, methyl ethyl ketone, ethyl acetate, butyl acetate, and nitromethane, preferably one or more of dichloromethane, toluene, ethyl acetate, butyl acetate and isopropyl acetate, more preferably comprising, preferably being, isopropyl acetate;

(i.1.2.4) admixing the solution obtained from (i.1.2.3) with an acidic aqueous system preferably comprising an acid which preferably comprises one or more of HCl, $H_2SO_4$, $HNO_3$, $NH_4Cl$, HCOOH, HOAc, said acid more preferably comprising, more preferably being, HCl;

(i.1.2.5) separating the aqueous phase from the organic phase;

(i.1.2.6) preferably extracting the aqueous phase, preferably with a solvent as defined in (i.1.2.3), more preferably with the solvent as defined in (i.1.2.3);

(i.1.2.7) drying the organic phases obtained from (i.1.2.5) and preferably (i.1.2.6), obtaining a purified compound of formula (IV).

92. The process of embodiment 90 or 91, preferably 91, comprising (i.1.2.8) further purifying the purified compound of formula (IV) obtained from (i.1.2.2), preferably from (i.1.2.7), wherein the further purifying preferably comprises column chromatography, more preferably silica gel column chromatography.

93. A compound of formula (III)

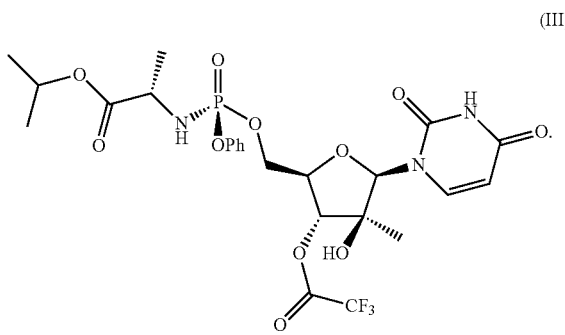

94. The compound of formula (III) according to embodiment 93, obtainable or obtained by a process according to any one of embodiments 46 and 47 to 92 insofar as embodiments 47 to 92 are dependent on embodiment 46.
95. A mixture comprising the compound of formula (III) according to embodiment 93 or 94 and a solvent, preferably an organic solvent, more preferably an aprotic organic solvent, wherein more preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran, wherein more preferably, the solvent comprises, preferably is, dichloromethane, preferably anhydrous dichloromethane.
96. The mixture of embodiment 95, comprising a fluorinating agent which preferably comprises, more preferably is, one or more of (diethylamino)difluorosulfonium tetrafluoroborate and difluoro(morpholino)sulfonium tetrafluoroborate.
97. The mixture of embodiment 96, comprising a fluorination promotor which preferably comprises, more preferably is, one or more of triethylamine trihydrofluoride (TEA 3HF), triethylamine dihydrofluoride (TEA 2HF), and diazabicycloundec-7-ene (DBU), preferably one or more of triethylamine trihydrofluoride and triethylamine dihydrofluoride.
98. Use of the mixture according to embodiment 96 or 97 for preparing a compound of formula (II)

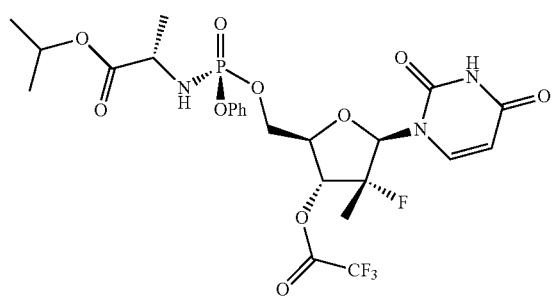

or for preparing a compound of formula (I)

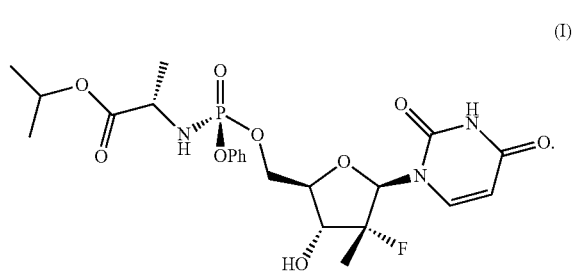 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

99. A compound of formula (IV)

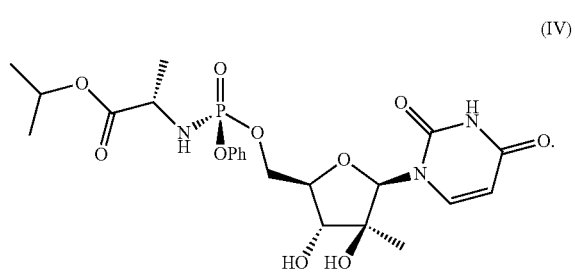 [SMILES: CC(C)OC(=O)[C@H](C)N[P@](=O)(OC[C@H]1O[C@@H](n2ccc(=O)[nH]c2=O)[C@@](C)(O)[C@@H]1O)Oc1ccccc1]

100. The compound of formula (IV) according to embodiment 99, obtainable or obtained by a process according to any one of embodiments 66 and 67 to 92 insofar as embodiments 67 to 92 are dependent on embodiment 66.
101. A mixture comprising the compound of formula (IV) according to embodiment 99 or 100 and a solvent, preferably an organic solvent, more preferably an aprotic organic solvent, wherein more preferably, the solvent comprises, preferably is, one or more of methylene chloride, methyl tert-butyl ether, tetrahydrofuran, dimethylsulphoxide, and dimethylformamide, wherein more preferably, wherein more preferably, the solvent comprises, preferably is, tetrahydrofuran.
102. The mixture of embodiment 101, comprising a hydroxyl group protecting agent, preferably Y—C(O)CF$_3$, more preferably trifluoroacetic anhydride.
103. Use of the mixture of embodiment 101 or 102 for preparing a compound of formula (III)

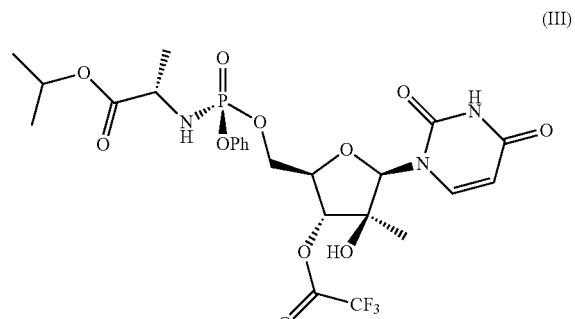

or for preparing a compound of formula (II)

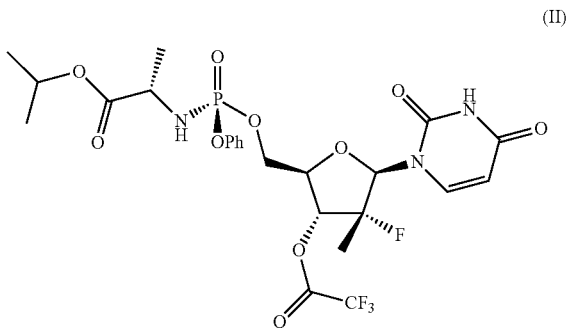 [SMILES: CC(C)OC(=O)[C@H](C)N[P@](=O)(OC[C@H]1O[C@@H](n2ccc(=O)[nH]c2=O)[C@](C)(F)[C@@H]1OC(=O)C(F)(F)F)Oc1ccccc1]
(II)

or for preparing a compound of formula (I)

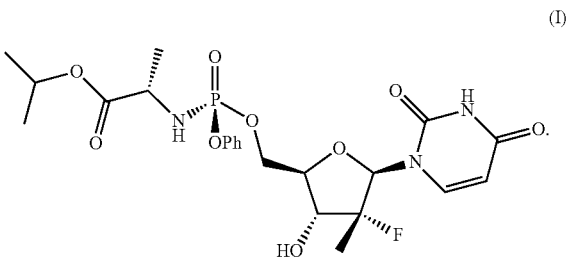 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]
(I)

104. A mixture comprising a compound of formula (II)

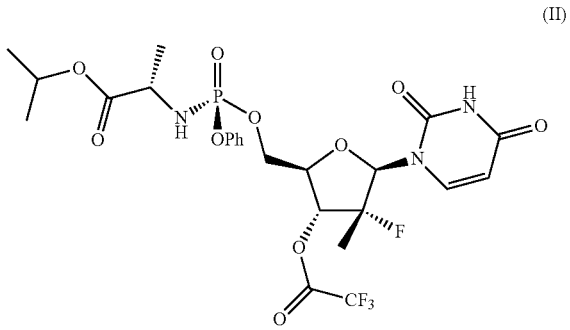 [SMILES: CC(C)OC(=O)[C@H](C)N[P@](=O)(OC[C@H]1O[C@@H](n2ccc(=O)[nH]c2=O)[C@](C)(F)[C@@H]1OC(=O)C(F)(F)F)Oc1ccccc1]
(II)

and a solvent, preferably an organic solvent, more preferably an aprotic organic solvent, wherein more preferably, the solvent comprises, preferably is, one or more of dichloromethane, dichloroethane, chloroform, toluene, acetone, acetonitrile, 1,4-dioxane, tetrahydrofuran (THF), methyl tetrahydrofuran, methyl tert-butyl ether, methyl ethyl ketone, ethyl acetate, butyl acetate, and nitromethane, preferably one or more of dichloromethane, dichloroethane, chloroform, toluene, tetrahydrofuran, methyl tert-butyl ether, 1,4-dioxane, and nitromethane, more preferably one or more of dichloromethane and tetrahydrofuran, wherein more preferably, the solvent comprises, preferably is, dichloromethane, preferably anhydrous dichloromethane.

105. A mixture comprising a compound of formula (V)

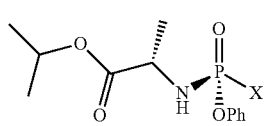
(V)

and a compound of formula (VI)

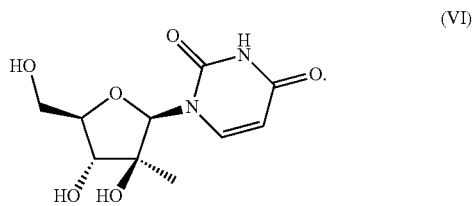 [SMILES: C[C@]1(O)[C@H](O)[C@@H](CO)O[C@H]1n1ccc(=O)[nH]c1=O]
(VI)

106. The mixture of embodiment 105, comprising a solvent, preferably an organic solvent, more preferably an aprotic organic solvent, wherein more preferably, the solvent comprises, preferably is, one or more of methylene chloride, methyl tert-butyl ether, tetrahydrofuran, dimethylsulphoxide, and dimethylformamide, wherein more preferably, wherein more preferably, the solvent comprises, preferably is, tetrahydrofuran.

107. The mixture of embodiment 105 or 106, comprising a Lewis acid which preferably comprises a twice positively charged ion or a three times positively charged ion, more preferably a twice positively charged metal ion or a three times positively charged metal ion, wherein the twice positively charged ion is preferably a Zn ion, a Mg ion, a Cu ion, or an Fe ion, more preferably a Zn ion, wherein more preferably, the Lewis acid comprises, preferably is, one or more of $ZnBr_2$, $ZnCl_2$, and $ZnI_2$, more preferably $ZnBr_2$.

108. The mixture of any one of embodiments 105 to 107, comprising a base, preferably an organic base, more preferably an organic nitrogenous base, wherein more preferably, the base comprises one or more of an amine, an amidine, and a heteroaromatic compound comprising a basic ring-nitrogen atom, more preferably one or more of ethyldiisopropylamine, triethylamine, diethylamine, 1,8-diazabicycloundec-7-ene, pyridine, quinoline, isoquinoline, acridine, pyrazine, imidazole, benzimidazole, and pyrazole, wherein more preferably, the base comprises, preferably is, triethylamine.

109. Use of the mixture according to any one of embodiments 105 to 108 for preparing a compound of formula (IV)

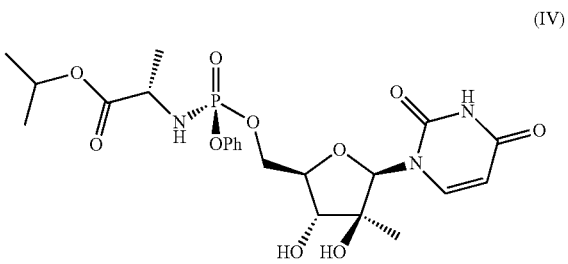 [SMILES: CC(C)OC(=O)[C@H](C)N[P@](=O)(OC[C@H]1O[C@@H](n2ccc(=O)[nH]c2=O)[C@@](C)(O)[C@@H]1O)Oc1ccccc1]
(IV)

or for preparing a compound of formula (III)

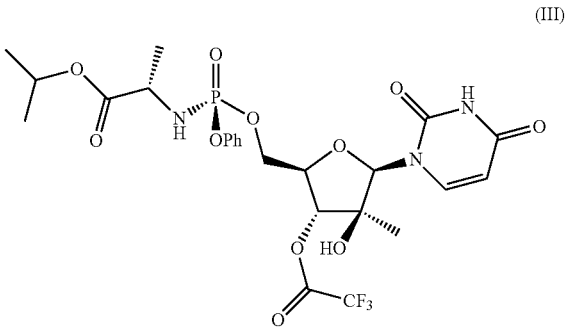 [SMILES: CC(C)OC(=O)[C@H](C)N[P@](=O)(OC[C@H]1O[C@@H](n2ccc(=O)[nH]c2=O)[C@@](C)(O)[C@@H]1OC(=O)C(F)(F)F)Oc1ccccc1]
(III)

or for preparing a compound of formula (II)

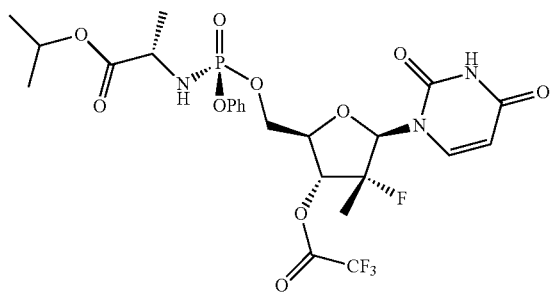

or for preparing a compound of formula (I)

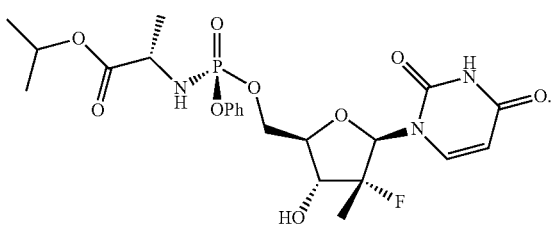

110. A mixture comprising a compound of formula (I)

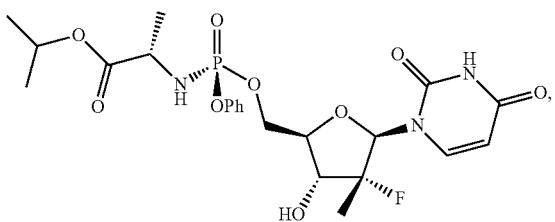

wherein said mixture is obtainable or obtained by step (iv) of a process according to any one of embodiments 33 to 39.

111. A compound of formula (I)

obtainable or obtained by a process according to any one of embodiments 10 to 92.

112. Use of the compound of embodiment 111 for the preparation of a pharmaceutical composition.

113. A method of using the compound of embodiment 112 for the preparation of a pharmaceutical composition.

114. A pharmaceutical composition, comprising the compound of embodiment 111 and preferably at least one pharmaceutically acceptable excipient.

115. The pharmaceutical composition of embodiment 111 for use in a method for treating hepatitis C in a human.

116. Use of the pharmaceutical composition of embodiment 114 or 115 for treating hepatitis C in a human.

117. A method of treating hepatitis C in a human comprising administering the pharmaceutical composition of embodiment 114 or 115 to a human.

118. Use of the compound of embodiment 111 for preparing a medicament for the treatment hepatitis C in a human.

119. Use of the compound of embodiment 111 for the treatment of hepatitis C in a human.

120. The compound of embodiment 111 for use in the treatment of hepatitis C in a human.

121. The compound of embodiment 111 for the treatment of hepatitis C in a human.

122. A method of treating hepatitis C in a human comprising administering the compound of embodiment 111 to a human.

The present invention is further illustrated by the following examples, comparative examples, and references examples.

EXAMPLES

List of Abbreviations

DCM dichloromethane
dr or d.r. diastereomeric excess
equiv equivalents
EtOH ethanol
HPLC high pressure liquid chromatography
M molar, molarity
MTBE methyl tert-butyl ether
NMR nuclear magnetic resonance
ppm parts per million
r.t. room temperature
TEA triethylamine
TFA trifluoroacetic acid
TFAA trifluoroacetic acid anhydride
THF tetrahydrofuran
TLC thin layer chromatography Reference Example 1: General Analytical Methods Reactions were monitored by HPLC on a C-18 reverse phase column with a gradient of acetonitrile in 10 mM ammonium sulfamate aqueous buffer at pH 5.6 or 40 mM aqueous sulfamic acid, or using thin layer chromatography (TLC) on silica gel pre-coated aluminum sheets (Silica gel 60 $F_{254}$, Merck). TLC visualization was accomplished by irradiation with UV light at 254 nm and/or a ceric ammonium molybdate stain. $^1$H and $^{13}$C chemical shifts are reported in ppm relative to TMS (0 ppm) with the solvent resonance as the internal standard (CDCl$_3$, $^1$H: 7.26 ppm, $^{13}$C: 77.16 ppm, (CD$_3$)$_2$O $^1$H: 2.05 ppm, $^{13}$C: 29.84, 202.26 ppm).

Example 1: Preparation of a Compound of Formula (I) (Sofosbuvir)

Example 1.1: Preparation of Compound of Formula (V)

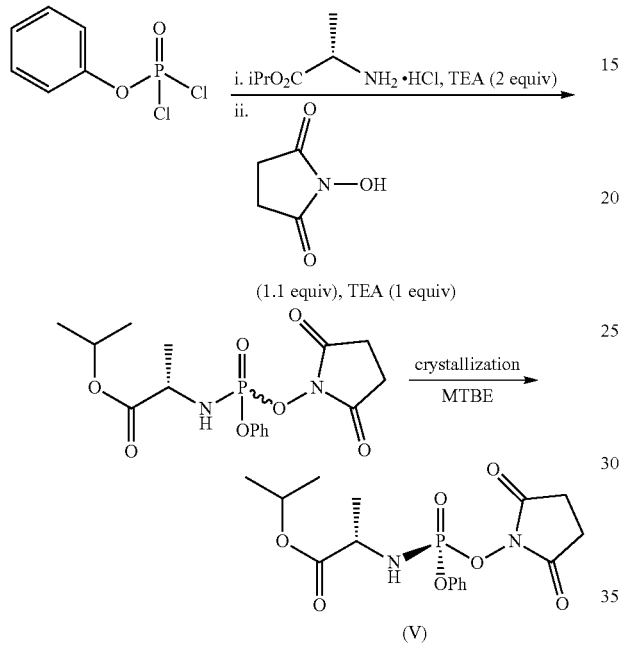

In a dry two-neck round bottom flask equipped with a mechanical stirrer and a dropping funnel was dissolved L-alanine isopropyl ester (20.0 g, 119 mmol, 1 equiv) in dichloromethane (125 mL) and the solution was cooled to −78° C. with a dry ice/acetone bath. To this solution, triethylamine (33 mL, 239 mmol, 2 equiv) was added via a dropping funnel with stirring, upon which a white precipitate was formed. Phenyl dichlorophosphate (17.8 mL, 119 mmol, 1 equiv) in dichloromethane (125 mL) was then added dropwise over 1 h, and the reaction mixture was stirred for 30 min at −75° C. and for 2 h at 0° C. In a separate flask, N-hydroxysuccinimide (13.68 g, 119 mmol, 1 equiv) was suspended in dichloromethane (75 mL) and charged with triethylamine (16.5 mL, 119 mmol, 1 equiv) upon which a solution was obtained. This solution was added to the main reaction vessel dropwise over 40 min. The reaction was allowed to warm up to room temperature and stirred overnight. The crude reaction mixture was filtered washing with dichloromethane and extracted with a 1:1 mixture of sat. aq. NH$_4$Cl and water (1×200 mL and 1×100 mL), followed by a 1:1 mixture of sat. aq. NaCl and water (1×100 mL). The organic phase was separated and the volatiles were removed under reduced pressure. The crude oil was dissolved in 160 mL MTBE and seeded with pure compound (V) and stirred, upon which a solid began to form slowly. The mixture was diluted with 100 mL of MTBE, warmed up until all of the solid dissolved and seeded with pure compound (V) again, upon which needle-like crystalline solid began to form slowly. The mixture was diluted with 100 mL MTBE and left to stand overnight, then stirred at 0° C. in an ice bath. The solid was filtered and dried to give 3.25 g diastereopure compound (V) (8.4 mmol, 7%).

$^1$H NMR (300 MHz, CDCl$_3$): 7.41-7.29 (m, 4H), 7.25-7.17 (m, 1H), 5.03 (sept, J=6.2 Hz, 1H), 4.29-4.13 (m, 1H), 4.09 (dd, J=11.2 Hz, 9.8 Hz, 1H), 2.78 (s, 4H), 1.44 (d, J=7.0 Hz, 3H), 1.26 (apparent t, J=6.65 Hz, 6H).

$^{13}$C NMR (75 MHz, CDCl$_3$): 173.0 (d, J=7.6 Hz), 169.4, 150.4 (d, J=7.5 Hz), 129.9, 125.7, 120.2 (d, J=5.1 Hz), 69.5, 50.6 (d, J=2.3 Hz), 25.6, 21.8 (J=2.8 Hz), 20.8 (d, J=5.6 Hz).

Example 1.2: Preparation of Compound of Formula (IV)

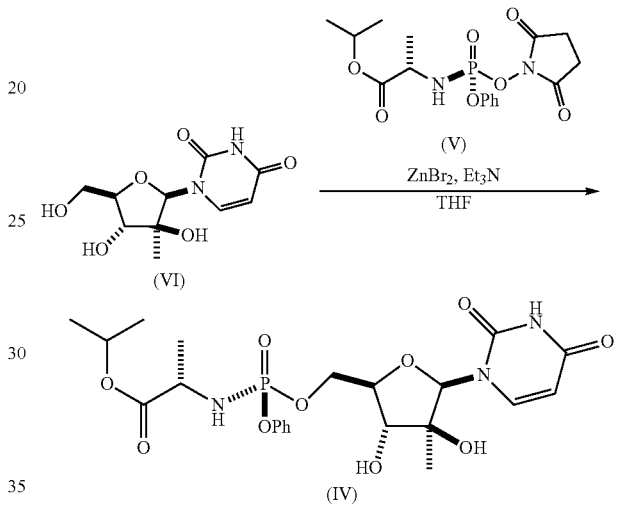

(S)-isopropyl 2-(((S)-(((2R,3R,4S,5R)-5-(2,4-dioxo-3,4-dihydropyrimidin-1(2H)-yl)-3,4-dihydroxy-4-methyltetrahydrofuran-2-yl)methoxy)(phenoxy)phosphoryl)amino)propanoate: In a two-neck round bottom flask purged with nitrogen, uridine derivative (VI) (obtained as described in Chemical and Pharmaceutical Bulletin, 1987, 35, page 2605) (2.5 g, 9.7 mmol) was dissolved in anhydrous THF (41.35 mL). To this solution 4 Angstrom molecular sieves (5 g) were added, followed by triethylamine (4.03 mL, 29.0 mmol, 3 equiv) and anhydrous ZnBr$_2$ (2.18 g, 9.7 mmol, 1 equiv). To this suspension, phosphoramidate (V) prepared according to Example 1.1 was added (4.7 g, 12.2 mmol, 1.2 equiv). The reaction was stirred for 20 h and filtered through a Nutsche filter, washing with THF (10 mL). The filtrate was evaporated under reduced pressure to dryness and taken up in isopropyl acetate (40 mL). To this solution, 1M HCl (40 mL) was added, and the phases were separated. The aqueous phase was re-extracted with isopropyl acetate (20 mL), and the combined organic phases evaporated to dryness. The resulting amorphous solid was purified by silica gel column chromatography, eluting with MTBE/EtOH (100:0 to 60:40 gradient) to obtain (IV) as a white amorphous solid (purest fraction: 2.16 g, 4.1 mmol, 42%, dr=88:12).

$^1$H NMR (300 MHz, DMSO): 11.30 (br s, 1H), 7.59 (d, J=8.1 Hz, 1H), 7.43-7.30 (m, 2H), 7.28-7.12 (m, 3H), 5.99 (dd, J=12.7 Hz, 10.1 Hz, 1H), 5.85 (s, 1H), 5.67 (d, J=5.1 Hz, 1H), 5.51 (d, J=8.1 Hz, 1H), 5.37 (s, 1H), 4.86 (sept, J=6.2 Hz, 1H), 4.29-4.15 (m, 2H), 4.01-3.64 (m, 3H), 1.31-1.09 (m, 12H).

Example 1.3: Preparation of Compound of Formula (I) (Sofosbuvir)

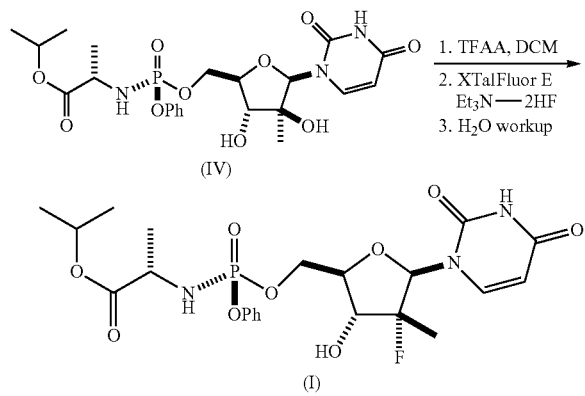

1. TFAA, DCM: In a two-neck round bottom flask purged with nitrogen, compound (IV) prepared according to Example 1.2 (100 mg, 0.189 mmol, 1 equiv) was dissolved in anhydrous DCM (2 mL). To this solution was added trifluoroacetic anhydride (28.1 microL, 0.199 mmol, 1.05 equiv), and the mixture was stirred at r.t. for 2 hours. Evaporation of the solvent and $^1$H NMR analysis indicated complete conversion of the starting material to the TFA-protected intermediate, the compound of formula (III) as described hereinabove which was obtained as a viscous oil.
2. XTalFluor E, Et$_3$N-2HF: The crude material was dissolved in anhydrous DCM (2 mL), and to this solution, 0.36M TEA·2HF solution in DCM (0.79 mL, 0.283 mmol, 1.5 equiv) [prepared as follows: in a 10 mL graduated cylinder filled with ca. 5 mL DCM, 400 microL TEA·3HF (2 equiv, Aldrich) was added, followed by triethylamine (171 microL, 1 equiv). The graduated cylinder was filled to the 10 mL mark and shaken. This solution was hygroscopic and used within one day] was added at r.t, followed by XTalFluor E (74 mg, 0.32 mmol, 1.7 equiv). The homogeneous reaction mixture was stirred at r.t. for 17 h, after which in-process control indicated full consumption of the starting material. The compound of formula (II) as described hereinabove and comprised in the mixture was not isolated.
3. H$_2$O workup: The crude mixture was diluted with DCM (10 mL) and extracted 1M HCl (5 mL). The aqueous phase was washed with DCM (10 mL), and the combined organic phases were dried over Na$_2$SO$_4$ and evaporated. HPLC analysis of crude reaction mixture indicated 67 area % of sofosbuvir of formula (I) (dr=91:9).
4. Purification: The crude material was taken up in DCM (1 mL), seeded with 4 mg crystalline (I) (prepared according to WO 2011/123645 A1, Example 10) and left to stir for 17 h. The precipitate was collected by filtration, washed with ice-cold DCM and dried to obtain (I) as a solid (44 mg, 44%).

Comparative Example 1: Fluorination According to Example 1.3, Step 2, of Unprotected Compound of Formula (IV)

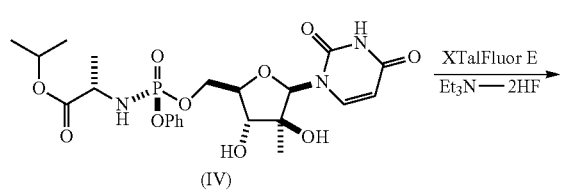

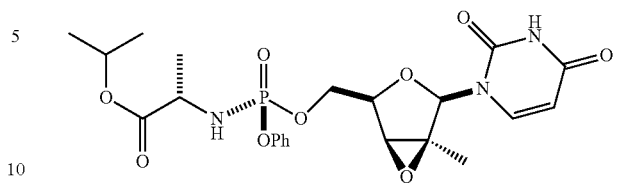

Compound (IV) prepared according to Example 1.2 (100 mg) was dissolved in anhydrous DCM (2 mL), and. To this solution, 0.36M TEA·2HF solution in DCM (0.79 mL, 0.283 mmol, 1.5 equiv) [prepared as follows: in a 10 mL graduated cylinder filled with ca. 5 mL DCM, 400 microL TEA·3HF (2 equiv, Aldrich) was added, followed by triethylamine (171 microL, 1 equiv). The graduated cylinder was filled to the 10 mL mark and shaken. This solution was hygroscopic and used within one day] was added at r.t, followed by XTal-Fluor E (74 mg, 0.32 mmol, 1.7 equiv). The homogeneous reaction mixture was stirred at r.t. for 1 h, after which in-process control indicated full consumption of the starting material. The crude mixture was diluted with DCM (10 mL) and extracted 1M HCl (5 mL). The aqueous phase was washed with DCM (10 mL), and the combined organic phases were dried over Na$_2$SO$_4$ and evaporated. HPLC analysis of crude reaction mixture indicated the formation of a new compound with m/z=510 [M+H]$^+$ most likely corresponding to the tertative structure shown above.

CITED PRIOR ART

WO 2008/121634 A
WO 2006/031725 A
J. Org. Chem. 2009, 74, 6819
WO 2010/135569 A
WO 2011/123645 A
WO2014/164533 A
Capon, B.; McManus, S. P. *Neighbouring Group Participation*; Plenum: New York, 1976, page 11
Capon, B. *Q. Rev. Chem. Soc.* 1964, 18, pp 45-111.
Chemical and Pharmaceutical Bulletin, 1987, 35, p 2605

The invention claimed is:
1. A process for preparing a compound of formula (I)

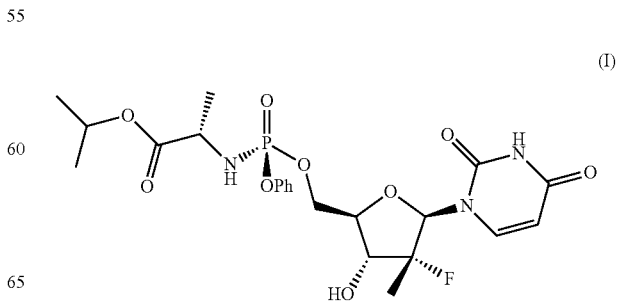

or a salt thereof, the process comprising
(i) providing a compound of formula (III)

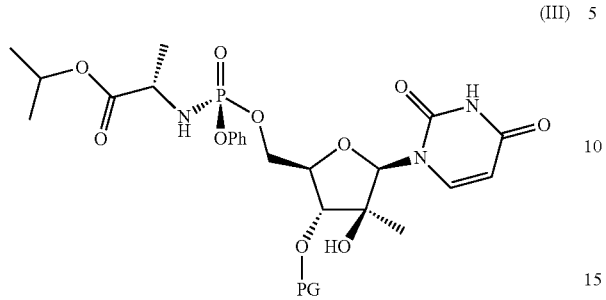

wherein PG is an inert electron withdrawing hydroxyl protecting group;
(ii) reacting the compound of formula (III) with a fluorinating agent, obtaining a compound of formula (II)

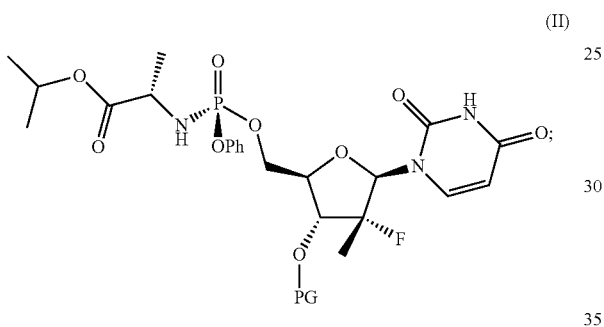

(iii) optionally isolating the compound of formula (II) from the reaction mixture obtained in (ii); and
(iv) deprotecting the compound of formula (II) obtaining the compound of formula (I).

2. The process of claim 1, wherein the inert electron withdrawing hydroxyl protecting group PG is $C(O)CH_nX_{3-n}$ with X being halogen and n being 0, 1, or 2.

3. The process of claim 1, wherein the fluorinating agent according to (ii) comprises one or more of (diethylamino)difluorosulfonium tetrafluoroborate and di-fluoro(morpholino)sulfonium tetrafluoroborate.

4. The process of claim 1, wherein according to (ii), the compound of formula (III) is reacted with the fluorinating agent in the presence of a fluorination promotor, wherein the fluorination promotor comprises one or more of triethylamine trihydrofluoride, triethylamine dihydrofluoride, and diazabicycloundec-7-ene.

5. The process of claim 1, wherein according to (ii), the compound of formula (III) is reacted with the fluorinating agent in a solvent.

6. The process of claim 1, wherein after (ii) and before (iv), the compound of formula (II) is not isolated from the reaction mixture obtained in (ii) and wherein the mixture obtained in (ii) is used as starting mixture for the deprotecting according to (iv).

7. The process of claim 1, wherein the deprotecting according to (iv) comprises
(iv.1) reacting the compound of formula (II) with an aqueous system, obtaining the compound of formula (I), wherein the aqueous system comprises water.

8. The process of claim 1, comprising
(v) purifying the compound of formula (I).

9. The process of claim 1, wherein according to (i), providing the compound of formula (III) comprises
(i.1) providing a compound of formula (IV)

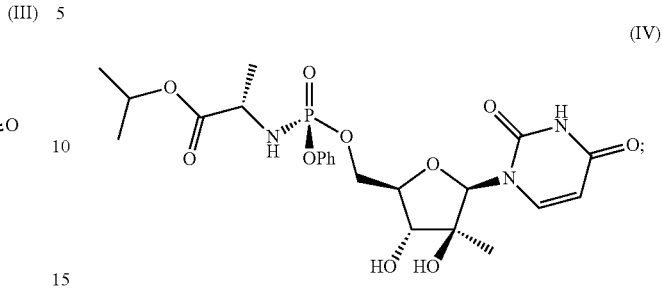

(i.2) reacting the compound of formula (IV) with a hydroxyl protecting agent Y-PG obtaining the compound of formula (III), wherein according to (i.2), the compound of formula (IV) is reacted with the hydroxyl protecting agent Y-PG.

10. The process of claim 9, wherein the reaction mixture obtained from (i.2) is directly employed in (ii).

11. The process of claim 9, wherein according to (i.1), providing the compound of formula (IV) comprises
(i.1.1) reacting a compound of formula (V)

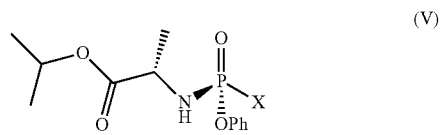

with a compound of formula (VI)

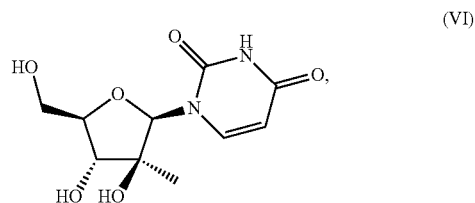 [SMILES: C[C@]1(O)[C@H](O)[C@@H](CO)O[C@H]1n1ccc(=O)[nH]c1=O]

obtaining the compound of formula (IV), wherein the residue X of the compound of formula (V) according to (i.1.1) is a leaving group which is suitable for a nucleophilic substitution reaction.

12. The process of claim 11, wherein according to (i.1.1), the compound of formula (V) is reacted with the compound of formula (VI) in the presence of a Lewis acid.

13. A compound of formula (III)

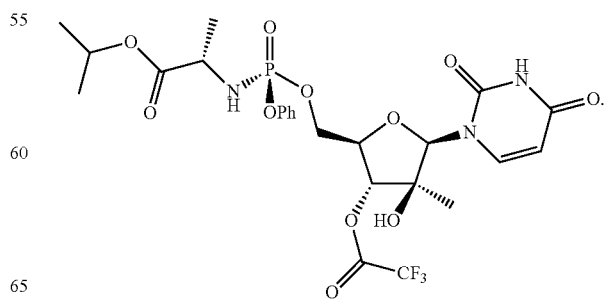

14. A compound of formula (IV)
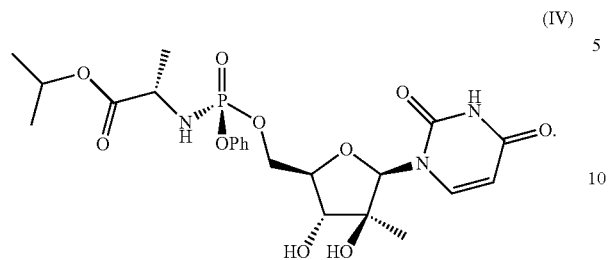
15. A mixture comprising a compound of formula (II)
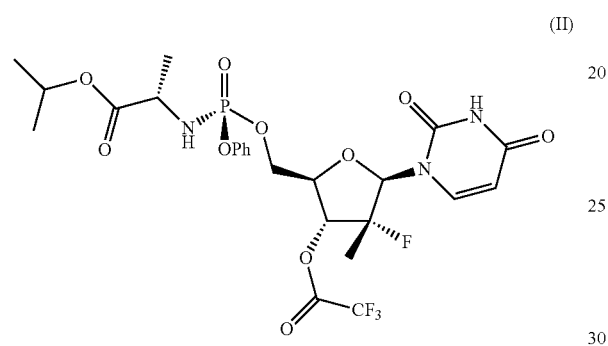
and a solvent.
* * * * *